United States Patent
Takahashi et al.

(10) Patent No.: US 6,324,480 B1
(45) Date of Patent: Nov. 27, 2001

(54) METHOD FOR ANALYZING FRICTION REDUCTION EFFECTS OF BUBBLES IN FRICTION-REDUCING SHIP

(75) Inventors: Yoshiaki Takahashi, Tokyo; Yuki Yoshida, Kawasaki; Hiroharu Kato, 5-31-9, Koganehara, Matsudo-shi, Chiba-ken, all of (JP)

(73) Assignees: Ishikawajima-Harima Heavy Industries Co., Ltd., Tokyo; Hiroharu Kato, Matsudo, both of (JP)

( * ) Notice: Subject to any disclaimer, the term of this patent is extended or adjusted under 35 U.S.C. 154(b) by 0 days.

(21) Appl. No.: 09/317,326

(22) Filed: May 24, 1999

(30) Foreign Application Priority Data

Jun. 3, 1998 (JP) .................................................. 10-155044

(51) Int. Cl.$^7$ ............................. G01F 17/00; G01F 23/00; G01N 11/00
(52) U.S. Cl. ........................................... 702/50; 114/67 A
(58) Field of Search ................................. 702/50, 43, 45, 702/100, 108, 127, 183; 114/62 A; 73/9

(56) References Cited

U.S. PATENT DOCUMENTS

| | | | | |
|---|---|---|---|---|
| 5,054,412 | * | 10/1991 | Reed et al. ........................ | 114/67 A |
| 5,575,232 | * | 11/1996 | Kato et al. ........................ | 114/67 A |
| 5,613,456 | * | 3/1997 | Kuklinski ........................... | 114/67 A |
| 5,967,071 | * | 10/1999 | Wipper .............................. | 144/67 A |
| 6,145,459 | * | 11/2000 | Takahashi et al. ................. | 114/67 A |
| 6,186,085 | * | 2/2001 | Kato et al. ........................ | 114/67 A |

* cited by examiner

Primary Examiner—Marc S. Hoff
Assistant Examiner—Demetrius Pretlow
(74) Attorney, Agent, or Firm—Pearne & Gordon LLP

(57) ABSTRACT

A method is provided for analyzing the effects of bubbles on skin-friction reduction in a ship cruising in a bubbly flow field. A shear stress decrement $\tau_t$ produced by a bubble in a flow field is obtained in a high frequency band region, in which a product of a bubble time-constant T and a turbulence frequency $\omega_L$ in a flow field is sufficiently greater than 1, based on a resistive force $\Delta R_y$ acting on a bubble derived from the bubble movements in a fluid flow direction along a ship surface and in a direction at right angles to a ship wall surface. Assuming that the shear stress a decrement is generated by a decrease in a gas mixing length, an expression for the operative wall constant $\kappa_1$ for bubbly flow including a parametric bubble diameter $d_b$ is derived. Based on an expression relating the operative wall constant $\kappa_1$ and a local friction factor $C_f$ in bubbly flow, and an expression relating the normal wall constant $\kappa$ in non-bubbly flow and a local friction factor $C_{f0}$ in non-bubbly flow, an analytical solution is obtained for a skin-friction ratio $C_f/C_{f0}$.

6 Claims, 15 Drawing Sheets

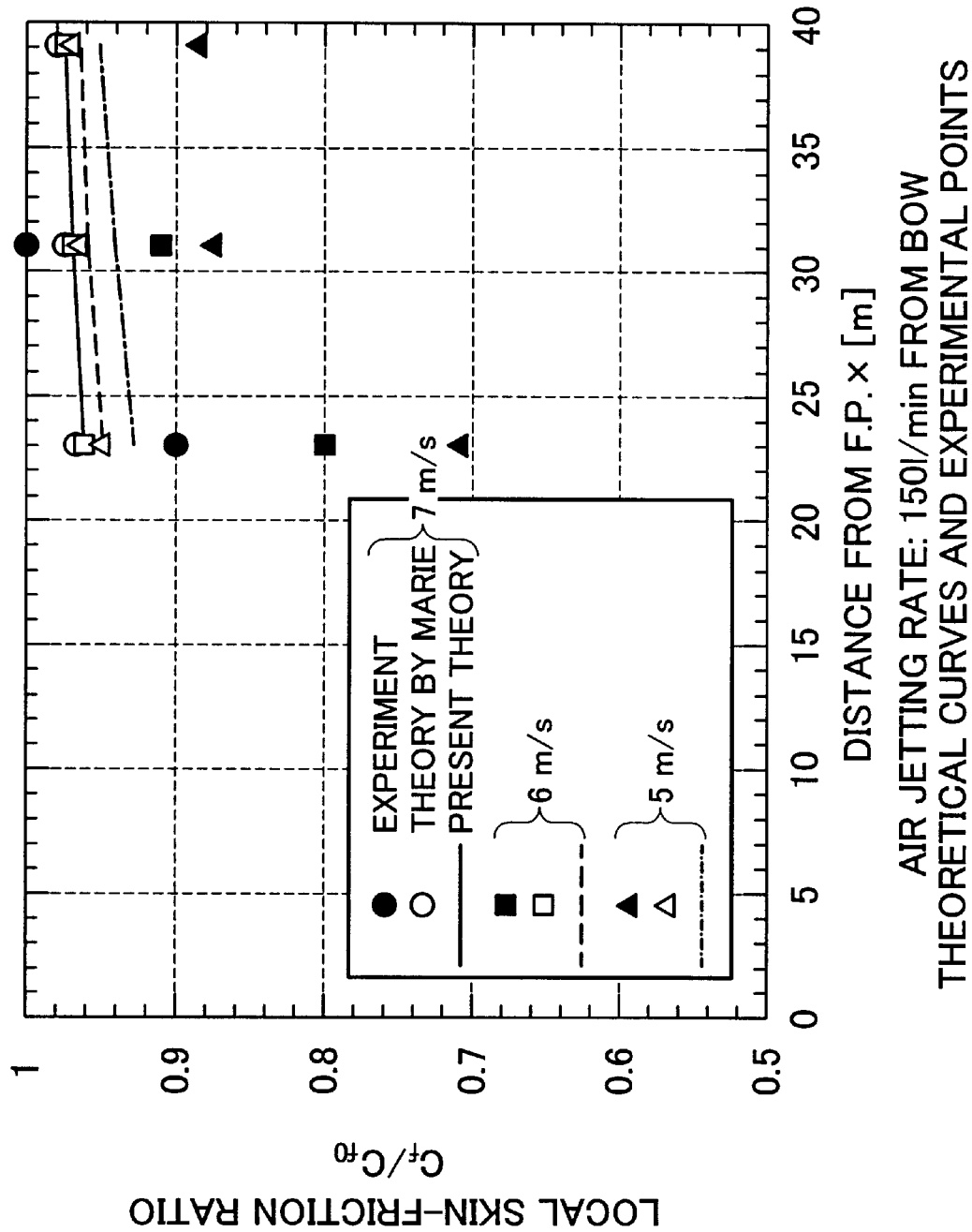

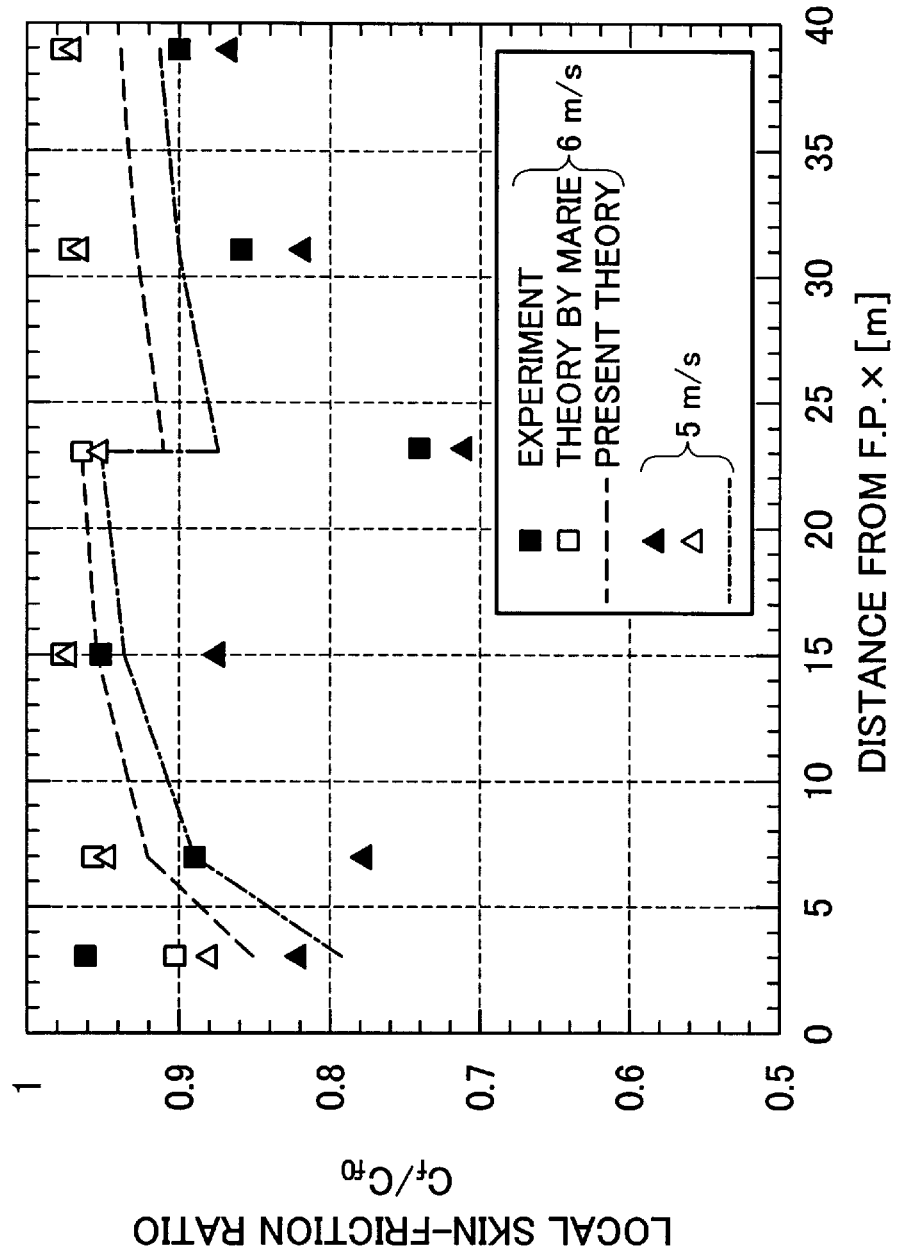

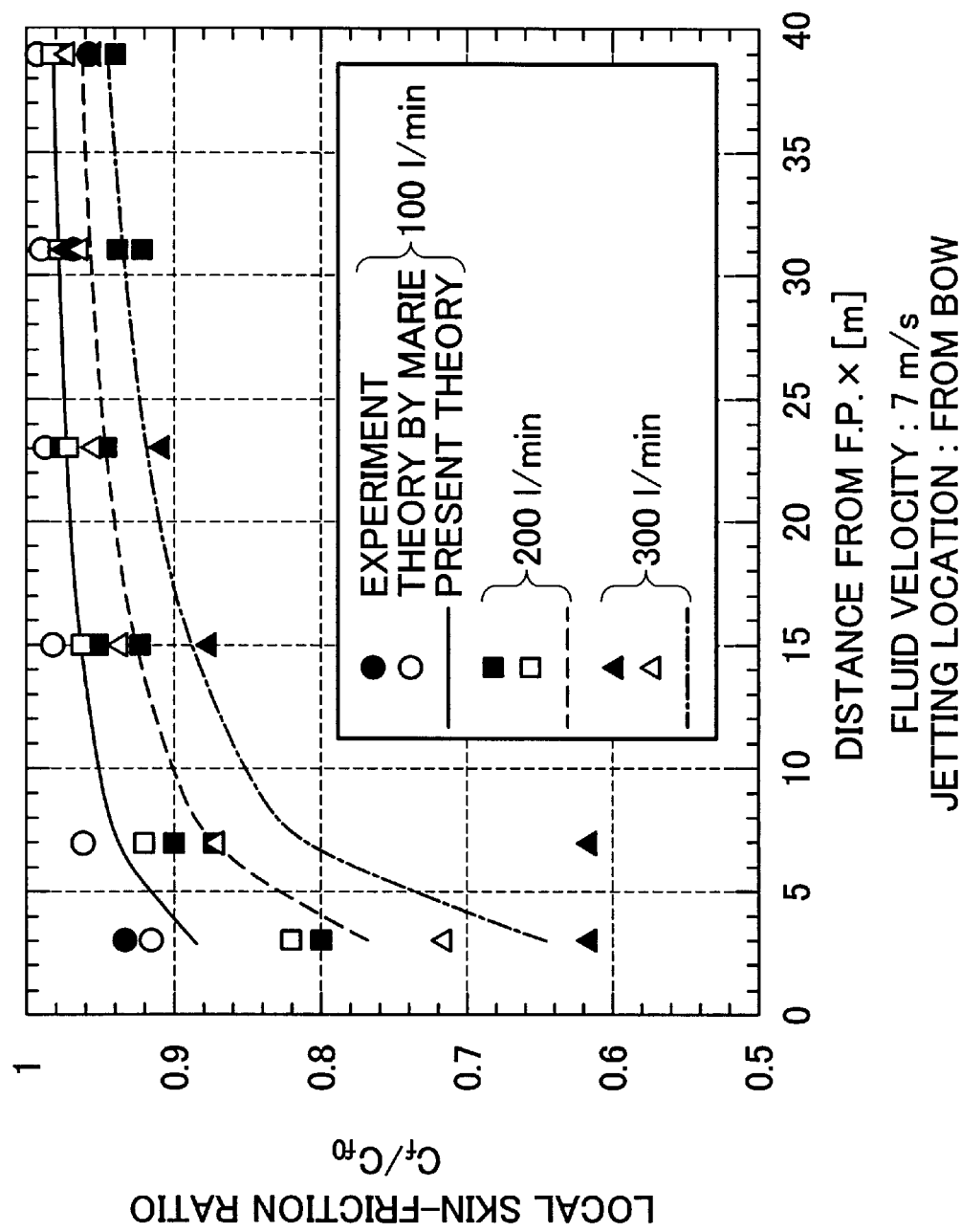

METHOD FOR ANALYZING FRICTION REDUCTION EFFECTS OF BUBBLES IN FRICTION-REDUCING SHIP

BACKGROUND OF THE INVENTION

1. Field of the Invention

The present invention relates to a method for analyzing the effects of interposing bubbles at the ship-water interface on reducing the skin-friction of a cruising ship.

2. Description of the Related Art

As a method for reducing skin-friction in a cruising ship, there is an approach of introducing bubbles in the outer surface region of the ship. Many theoretical models for analyzing the effects of bubbles in reducing the skin-friction assume that a void fraction distribution (distribution of bubbles in the boundary layer) is known before calculating various flow parameters in the flow fields surrounding the ship, therefore, it is essential to clarify the mechanism of producing the void fraction distribution to provide an accurate estimation of friction reduction effects. To apply such a friction reduction method to analysis of bubbly flow effects on an actual ship, it becomes necessary to estimate, during the course of computing various parameters in a flow field, the void fraction from a given volume of bubbles being supplied. Therefore, study of void fraction distribution is also critical from the viewpoints of practical application of bubbly flow for reducing the skin-friction.

The present inventors had disclosed an analytical method for obtaining dynamics of bubbles on the hull surface based on the mixing length theory, in a Japanese Patent Application, First Publication, Hei 8-144646. This was followed by a Japanese Patent Application, First Publication, Hei 9-292999, in which a technique was disclosed to simulate the bubble distribution patterns on hull surfaces. It was further disclosed in Japanese Patent Applications, First Publications, Hei 9-142818 and Hei 10-55453 (U.S. patent application Ser. No. 078,950) that a turbulent flow model in the turbulent boundary layer near the hull surface can be constructed by extending the mixing length theory to a bubbly flow field in the turbulent flow model, it offered an analytical methodology to logically explain past experimental results, and demonstrated that the friction reduction effects in different flow fields can be analytically reproduced, by adjusting the operative wall constant $\kappa_1$ in the wall law for bubbly flow to indicate the bubble mixing length, in accordance with the extent of flow fields, i.e., the thickness of the turbulent boundary layer produced.

However, in the technique disclosed in the aforementioned Japanese Patent Applications, First Publications, Hei 9-142818 and Hei 10-55453, emphasis was on simplifying the analytical process so that there were aspects of the model which were not fully examined in developing the theoretical framework. For example, it was considered that the following points need to be examined more closely in the future.

(1) Although bubble movement in y-direction (gravitational direction) was discussed quantitatively, it has not been made clear why the bubble can be assumed to remain stationary in x-direction (fluid flow direction) of the turbulent flow. Also, a question was unresolved as to the assumption of a constant magnitude of slip.

(2) When introducing an apparent the mixing length change $l_{mb}$, it was necessarily, for mathematical simplification, to suppose that either of the two turbulent flow velocities $u'_L$, $v'_L$ becomes completely zero and the other becomes affected by damping. In other words, a question remained in the assumption that the fluid shear decrement $\tau_t$ caused by a bubble is given by changes in the turbulent stress (Reynolds stress).

(3) Empirically, a wall constant $\kappa_1$ for bubbly flow (a constant in the wall law when a micro-bubble is present in the turbulent layer) was assumed to decrease in proportion to $(\lambda_m/d_b)\alpha^{2/3}$, where $\lambda_m$ is an apparent turbulence scale, $d_b$ is a bubble diameter and $\alpha$ is a local void fraction. But, it was unclear whether the operative wall constant $\kappa_1$ would be negative at very small $d_b$, and similarly, whether $\kappa_1$ would be negative at low $\lambda_m$.

(4) It was thought reasonable to assume that $\lambda_m v_L/U_\tau$ (=$y/y^+$), (proportional to the length of the bottom surface) where $v_L$ is the dynamic viscosity of liquid and $U_\tau$ is a the frictional velocity, but a question remained whether it is reasonable to assume that $y/y^+ \delta$ where $\delta$ is the thickness of the turbulent boundary layer.

(5) It was assumed that mixing of a bubble reduces friction, but was not certain that this was sufficient. Is there not a need to consider an increment in the shear stress caused by kinetic mass exchange resulting from motion of the bubble?

SUMMARY OF THE INVENTION

It is an object of the present invention to provide a mathematical model to yield a superior analysis of the effects of bubbly flow on reducing the skin-friction in a cruising ship.

The object has been achieved in a method for analyzing effects of generating bubble jets in a flow field near a ship surface on reducing skin-friction in a cruising ship comprising the steps of: obtaining a shear stress decrement $\tau_\tau$ produced by having a bubble in the flow field in terms of a resistive force $\Delta R_v$ acting on the bubble derived from movements of the bubble in a fluid flow direction, x-direction, along the cruising ship as well as in a direction at right angles to a ship wall surface, y-direction, in accordance with a definition of a high frequency band region in which a product of a bubble time-constant T and a turbulence frequency $\omega_L$ in the flow field is greater than 1; obtaining an operative wall constant $\kappa_1$ in the wall law when there is a bubble having a parametric bubble diameter $d_b$, by assuming that the shear stress decrement is generated by a decrease in a mixing length; and obtaining a solution for skin-friction ratio, $C_f/C_{f0}$, in the high frequency band region, according to an expression relating the operative wall constant $\kappa_1$ to a local friction factor $C_f$ for bubbly flow, and an expression relating a normal wall constant $\kappa$ in the wall law in non-bubbly flow to a a local friction factor $C_{f0}$ in non-bubbly flow.

The object has also been achieved in a method for analyzing effects of generating bubble jets in a flow field near a ship surface on reducing skin-friction in a cruising ship comprising the steps of: performing a Fourier transform of kinetic equations (1) and (2) for a bubble moving in x- and y-directions, representing a fluid flow direction and a direction at right angles to the ship surface, respectively, in terms of an added mass of a bubble $m_A$, a bubble diameter $d_b$, a dynamic liquid viscosity coefficient $v_L$, and obtaining an expression for a gain in x-direction $G_x$ and an expression for a gain in y-direction $G_y$ comprised by a bubble time-constant T and a turbulence frequency $\omega_L$, based on equations (3) and (4) respectively; obtaining from equation (16) a resistive force $\Delta R_v$ acting on a bubble in a high frequency band region where a product of a bubble time-constant T and a turbulence frequency $\omega_L$ is greater than 1, in terms of a normal wall constant $\kappa$ in the wall law in non-bubbly flow, a fluid density $\rho_L$, a dynamic fluid viscosity coefficient $v_L$, and a time-averaged velocity in x-direction $u_L$, by assuming that a turbulence cycle $2\pi/\omega_L$ in the flow field is equal to the integral time-scale $T_{*L}$; obtaining a shear stress decrement $\tau_t$ caused by the resistive force $\Delta R_v$ from equation (17); obtaining a mixing length decrement $l_{mb}$ from equation (27) in terms of an empirical constant $\alpha$, a bubble diameter $d_b$, a dynamic viscosity coefficient $\alpha_L$, a frictional velocity $U_\tau$ and a near-wall local void fraction $\alpha_W$, by comparing the equation (17) with equation (22) which expresses a shear stress decrement $\tau_t$ that is assumed to be produced by a mixing length decrement $l_{mb}$; obtaining a revising wall constant $\kappa_2$ in the wall law as in equation (33) by using the equation (27), and obtaining an expression as in equation (34) for an operative wall constants $\kappa_1$ for bubbly flow in terms of the empirical constant $\alpha$ and the bubble diameter $d_b$ as parameters, by subtracting the revising wall constant $\kappa_2$ from the normal wall constant $\kappa$, deriving equation (36) for non-bubbly flow and equation (40) for bubbly flow, assuming that a fluid velocity distribution obeys a logarithmic law, and assuming that a position parameter y is represented by a turbulent boundary layer thickness $\delta$, obtaining corresponding equation (44) relating the normal wall constant $\kappa$ to a local friction factor $C_f$ in bubbly flow, and equation (45) relating the operative wall constants $\kappa_1$ to a local friction factor $C_{f0}$ in non-bubbly flow; subtracting the equation (44) from the equation (45) to obtain equation (48), and expanding a series expression $(C_f/C_{f0})^{1/2}$ in equation (48) about 1 so as to derive equation (49) comprised by first-order expansion terms while also expanding a bottom-layer term $v_L/U_{\tau\tau}$ in the equation (48) for an operative wall constants $\kappa_1$ for bubbly flow, thereby deriving equation (50); and obtaining an analytical solution (55) for skin friction ratio $C_f/C_{f0}$ in the high frequency band region by substituting the equation (50) in the equation (33) to yield a first result and substituting the first result into the equation (34) to yield a second result and substituting the second result into the equation (49) and solving to obtain an expression for the analytical solution (55); wherein the equations referenced above are listed as follows;

$$\frac{m_A}{3\pi\mu_L d_b}\ddot{X} + \dot{X} = u'_L \tag{1}$$

$$\frac{m_A}{3\pi\mu_L d_b}\ddot{Y} + \dot{Y} = v'_L \tag{2}$$

$$\frac{\hat{\dot{X}}}{\hat{u}'_L} = \frac{1}{\sqrt{1+T^2\omega_L^2}} = G_X \tag{3}$$

$$\frac{\hat{Y}}{\hat{v}'_L} = \frac{1}{\sqrt{1+T^2\omega_L^2}}\frac{1}{\omega_L} = G_Y \tag{4}$$

$$\Delta\hat{R}_v = \frac{27}{4\pi}\kappa\rho_L(\varepsilon_L T_{*L})^2\left(\frac{\partial\overline{u}_L}{\partial y}\right)^2 \tag{16}$$

$$\tau_t = \frac{81}{\pi^2}\kappa\rho_L\left(\frac{v_L T_{*L}}{d_b}\right)^2\alpha_w\left(\frac{\partial\overline{u}_L}{\partial y}\right)^2 \tag{17}$$

$$\tau_t = 2\rho_L l_{mo} l_{mb}\left(\frac{\partial\overline{u}_L}{\partial y}\right)^2 \tag{22}$$

$$l_{mb} = \left(\frac{v_L/U_\tau}{d_b/a}\right)^2 \alpha_w y \tag{27}$$

$$\kappa_2 = \left(\frac{v_L/U_\tau}{d_b/a}\right)^2 \alpha_w \tag{33}$$

$$\kappa_1 = \kappa - \kappa_2 \tag{34}$$
$$= \kappa - \left(\frac{v_L/U_\tau}{d_b/a}\right)^2 \alpha_w$$

$$u_0^+ = \frac{1}{\kappa}\log y_0^+ + B \text{ where } B \text{ is a constant} \tag{36}$$

$$u^+ = \frac{1}{\kappa_1}\log y^+ + B \tag{40}$$

$$\sqrt{\frac{2}{C_{f0}}} = \frac{1}{\kappa}\log\delta_0^+ + B \tag{44}$$

$$\sqrt{\frac{2}{C_f}} = \frac{1}{\kappa_1}\log\sqrt{\frac{C_f}{C_{f0}}}\delta_0^+ + B \tag{45}$$

$$\sqrt{\frac{2}{C_{f0}}}\sqrt{\frac{C_{f0}}{C_f}} - \sqrt{\frac{2}{C_{f0}}} = -\frac{1}{\kappa_1}\log\sqrt{\frac{C_{f0}}{C_f}} + \left(\frac{1}{\kappa_1} - \frac{1}{\kappa}\right)\log\delta_0^+ \tag{48}$$

-continued $$\sqrt{\frac{2}{C_{f0}}}\sqrt{\frac{C_{f0}}{C_f}} - \sqrt{\frac{2}{C_{f0}}} = -\frac{1}{\kappa_1}\left(1 - \sqrt{\frac{C_{f0}}{C_f}}\right) + \left(\frac{1}{\kappa_1} - \frac{1}{\kappa}\right)\log\delta_0^+ \quad (49)$$

$$\frac{v_L}{U_\tau} = \frac{v_L}{U}\sqrt{\frac{2}{C_f}} = \sqrt{\frac{C_{f0}}{C_f}}\frac{v_L}{U}\sqrt{\frac{2}{C_{f0}}} \quad (50)$$

$$\frac{C_f}{C_{f0}} = \left\{\frac{1 + \sqrt{2/C_{f0}}\,\kappa_{10} - 2(\log\delta_0^+)\kappa_{20}/\kappa}{1 + \sqrt{2/C_{f0}}\,\kappa_{10} - (\log\delta_0^+)\kappa_{20}/\kappa}\right\}(1 - \alpha_w) \quad (55)$$

By adopting such methods, it is possible to improve the accuracy of analyzing the effects of bubbles in reducing the skin-friction in a cruising ship.

BRIEF DESCRIPTION OF THE DRAWINGS

FIG. 15 is a second graph showing the results of verification of the second embodiment.

FIG. 16 is a third graph showing the results of verification of the second embodiment.

FIG. 17 is a fourth graph showing the results of verification of the second embodiment.

DESCRIPTION OF THE PREFERRED EMBODIMENTS

Preferred embodiments will be explained in detail in the following with reference to the drawings presented above.

First Embodiment

The turbulent flow model in the first embodiment will be explained first.

1. Turbulent Flow Model

Figure 1:
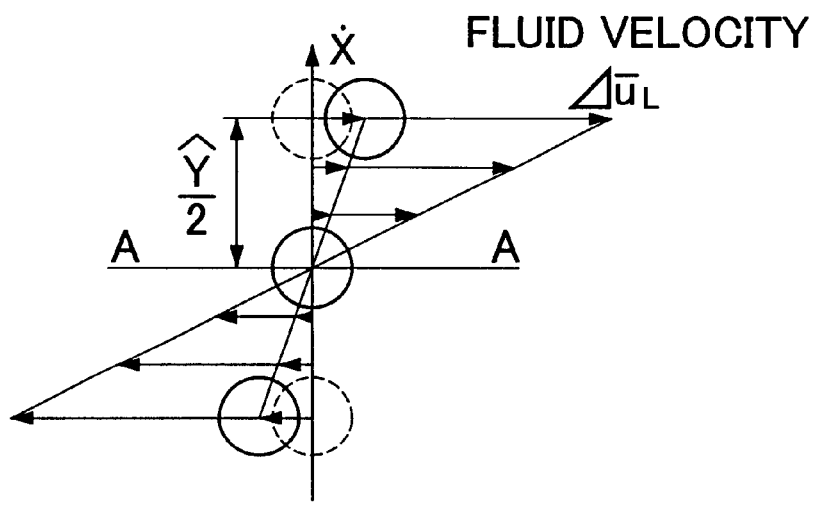
FIG. 1 is a conceptual drawing of the turbulent flow model in a first embodiment.

As shown in FIG. 1, this embodiment presents analyses of bubbly flow in a boundary layer beneath a two-dimensional plate (for example, the bottom surface of a ship) in terms of a turbulent flow model which includes y-direction and x-direction at right angles to the y-direction. In other words, movements of the bubbles ejected from the hull surface (bottom wall surface) will be analyzed in the perpendicular direction to the wall surface (y-direction) and in the fluid flow direction along the hull surface (x-direction).

A Bubbles ejected into the turbulent flow layer will move in response to the velocity of turbulent flow of the liquid phase. Density of air is about $1/10^3$ of that for water, and its momentum is negligibly small compared with the added inertial force. However, because of the added inertial force, the ejected bubbles do not respond immediately to the fluid velocity, and a differential velocity is produced between the air and liquid phases. The differential velocity creates a resistive force on the bubble, and a reactive force in the liquid phase. In order to compute the differential velocities in the air/liquid phases, it is necessary to comprehend the dynamic properties of the bubble motion that can be analyzed in terms of the kinetic equations of motion.

Certain assumptions are made in deriving the kinetic equations. It is assumed that the bubble is spherical, the added mass of the bubble is ½ of an equivalent mass of water, the resistive force is derived from the Stokes equations. Under these premises, motion of the bubble is analyzed with respect to an origin of a simple time-averaged position of the liquid particles flowing along a path A—A shown in FIG. 1, producing displacements X, Y. The kinetic equations of motion of the bubble are as follows:

$$\frac{m_A}{3\pi\mu_L d_b}\ddot{X} + \dot{X} = u'_L \quad (1)$$

and $$\frac{m_A}{3\pi\mu_L d_b}\ddot{Y} + \dot{Y} = v'_L \quad (2)$$

where $m_A$ is an added mass of a single bubble, $\mu_L$ is the viscosity coefficient of the liquid phase, $d_b$ is the diameter of the bubble, $u'_L$ is the turbulent velocity of the liquid in x-direction, $v'_L$ is the turbulent velocity of the liquid in y-direction, the superscript ' refers to a change from an instantaneous average velocity (turbulent velocity) and the subscript L indicates that the property relates to the liquid phase.

By subjecting these equations (1) and (2) to a Fourier transform, squared average gains of the relative displacement velocities in x- and y-directions corresponding to the squared average turbulent velocities in x- and y-directions can be obtained using equations (3) and (4) shown below. In these equations, a bar-crown indicates time-averaging and a circumflex-crown ^, for example, denotes a squared average value.

$$\frac{\hat{X}}{\hat{u}_L'} = \frac{1}{\sqrt{1+T^2\omega_L^2}} = G_X \quad (3)$$

$$\frac{\hat{Y}}{\hat{v}_L'} = \frac{1}{\sqrt{1+T^2\omega_L^2}} \frac{1}{\omega_L} = G_Y \quad (4)$$

where $\omega_L$ refers to the angular frequency of the turbulent flow in a flow field, T a time-constant for a bubble which is given by equation (5) given below.

$$T = \frac{m_A}{3\pi\mu_L d_b} = \frac{d_b^2}{36\nu_L} \quad (5)$$

where $\nu_L$ is the dynamic viscosity of the liquid phase.

When considering squared averaging of time-based variables, squared average values are assumed to be the representative value. For example, when the bubble exists in the upper half region of the path A—A, squared average value for the resistive force $\Delta R_\nu$ for the bubble is expressed by equation (6) given below.

$$\Delta \hat{R}_\nu = 3\pi\mu_L d_b \left( \Delta \bar{u}_L - \hat{X} \right) \quad (6)$$

$$= 3\pi\mu_L d_b \left( \frac{\hat{Y}}{2} \frac{\partial \bar{u}_L}{\partial y} - G_X \hat{u}_L' \right)$$

$$= \frac{3}{2}\pi\mu_L d_b \left( \hat{Y} \frac{\partial \bar{u}_L}{\partial y} - G_X \hat{Y} \frac{\partial \bar{u}_L}{\partial y} \right)$$

$$= \frac{3}{2}\pi\mu_L d_b \hat{v}_L' (1 - G_X) G_Y \frac{\partial \bar{u}_L}{\partial y}$$

From equations (3) and (4), the term $G_Y$ in equation (6) is expressed as in equation (7) below:

$$(1-G_X)G_Y = \left( 1 - \frac{1}{\sqrt{1+T^2\omega_L^2}} \right) \frac{1}{\sqrt{1+T^2\omega_L^2\omega_L}} \frac{1}{\omega_L} \quad (7)$$

Here, depending on the order of magnitude of the time-constant T and the size of the turbulence cycle $2\pi/\omega_L$, three ranges of frequency band are considered. As indicated above, the bubble in this embodiment is assumed to be small enough to retain a spherical shape, but its motion is further considered under the following conditions:

low frequency band region: $T\omega_L 21 <1$ (8)
middle frequency band region: $T\omega_L = O(1)$ (9)
high frequency band region: $T\omega_L 22 >1$ (10).

The regions given by these conditional relations (8)-(10) are defined as low frequency band region, middle frequency band region and high frequency band region, respectively. Motions in the middle frequency band region are most complex to solve and require rigorous solutions based on actual operating conditions. If prominent frequencies are known, they may be solved by series expansion and other techniques, but this region is not dealt with in this embodiment. On the other hand, structural equations in the low or high frequency band regions are simpler to treat so that parametric dependency can be better anticipated in many cases. Therefore, the following presentation will be concerned only with the low and high frequency band regions.

1.1 High-frequency Band Region

In this region, $T\omega_L$ is much greater than 1, and in such a case, $(1-G_X)G_Y$ can be approximated by equation (11) based on the definition given in equation (10):

$$(1-G_X)G_Y = \frac{1}{T\omega_L^2} = \frac{36\nu_L}{d_b^2\omega_L^2} \quad (11)$$

Substituting equation (11) in equation (6) and denoting the density of liquid by $\rho_L$, and using a known relationship $\mu_L = \rho_L \nu_L$ between viscosity coefficient $\nu_L$ and $\rho_L$, squared average value of resistive force $\Delta R_\nu$ is given by equation (12):

$$\Delta \hat{R}_\nu = 54\pi\rho_L \nu_L^2 d_b^{-1} \omega_L^{-2} \hat{v}_L' \frac{\partial \bar{u}_L}{\partial y} \quad (12)$$

$$= 54\pi\rho_L \nu_L^2 d_b^{-1} \omega_L^{-2} l_{mo} \left( \frac{\partial \bar{u}_L}{\partial y} \right)^2$$

where $l_{mo}$ is the mixing length corresponding to the mean free path of a near-wall bubble. Strictly speaking, however, $l_{mo}$ does not correspond exactly to the mean free path of a bubble, because the apparent mixing length is affected by the amount of decrement in the shear stress caused by the resistive force of the bubble.

Figure 2:
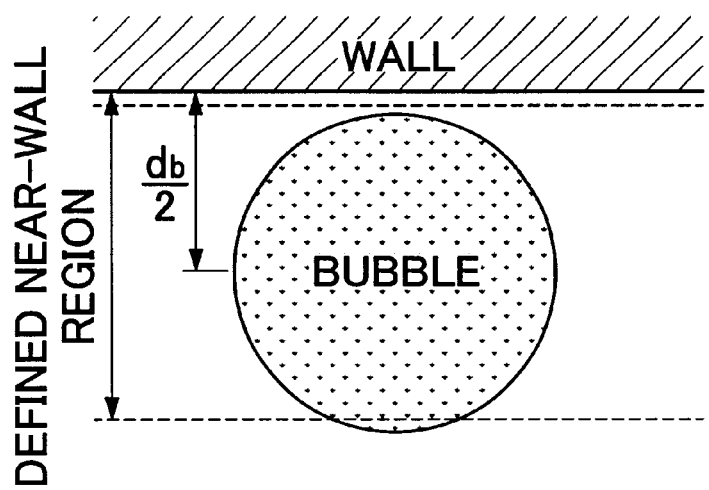
FIG. 2 is a schematic drawing of a near-wall bubble in a flow field in the first embodiment.

The range of near-wall distance is shown in FIG. 2 where the diameter of a air bubble do defines the extent of this distance from the wall, and the representative distance is taken at $y=d_b/2$.

The magnitude of the gas mixing length $l_{mo}$ in the near-wall region is given by equation (13).

$$l_{mo} \approx \kappa y \quad (13)$$

where $\kappa$ is a normal wall constant when a bubble is not present (von Karman constant) and a value of 0.41 is adopted.

Substituting $y=d_b/2$ in equation (13), equation (14) is obtained.

$$l_{mo} \approx \kappa \left( \frac{d_b}{2} \right) = \frac{1}{2}\kappa d_b \quad (14)$$

In the meantime, the turbulence cycle $2\pi/\omega_L$ can be assumed to be equal to the time duration $T_{*L}$ (integral time scale) required for a vortex to pass through a given point, so that equation (15) can be established.

$$\omega_L^{-2} = \frac{T_{*L}^2}{4\pi^2} \quad (15)$$

Therefore, squared average of the resistive force $\Delta R_\nu$ is obtained by substituting equations (14) and (15) in equation (12) to derive equation (16).

$$\Delta \hat{R}_\nu = \frac{27}{4\pi}\kappa \rho_L (\nu_L T_{*L})^2 \left( \frac{\partial \bar{u}_L}{\partial y} \right)^2 \quad (16)$$

An average length for one bubble in its spatial element (that is, an average length of free movement for one bubble on the wall surface) can be expressed as $(\pi/6\, \alpha_w)^{1/2}d_b$ for a given void fraction $\alpha_w$ so that the shear stress decrement $\tau_t$ caused by the resistive force of the bubble is expressed as in equation (17).

$$\tau_t \frac{81}{\pi^2}\kappa\rho_L\left(\frac{v_L T_{*L}}{d_b}\right)^2 \alpha_w\left(\frac{\partial \bar{u}_L}{\partial y}\right)^2 \tag{17}$$

Here, the shear stress should include an increment factor, as well as a decrement factor, caused by kinetic mass exchange taking place between the water and the bubble. It can be considered that when a bubble moves in the fluid, water of the equal volume flows into the space vacated by the bubble. Therefore, the movement of a bubble in the turbulent boundary layer can be considered to be equivalent to an added movement of water of the same volume. The mechanism of additional stress generation is the same as the Reynolds stress generated by the movement of liquid particles, therefore, shear stress increment $\tau_m$ cab be expressed as in equation (18).

$$\tau_m = \rho_L \hat{X}\hat{Y}\alpha_w \tag{18}$$

$$= \rho_L \frac{1}{1+T^2\omega_L^2}\frac{1}{\sqrt{1+T^2\omega_L^2}}\frac{1}{\omega_L}\alpha_w \hat{v}_L'^2 \frac{\partial \bar{u}_L}{\partial y}$$

In the high frequency band region defined by equation (10), the increment $\tau_m$ is given by equation (19).

$$\tau_m = \frac{\rho_L}{T^3\omega_L^4}\alpha_w \hat{v}_L'^2 \frac{\partial \bar{u}_L}{\partial y} \tag{19}$$

Comparing the shear stress increment $\tau_m$ given by equation (19) and the shear stress decrement $\tau_t$ given by equation (17), in the case of the high frequency band region defined by equation (10), it can be seen the term $1/T\omega_L$ in the increment $\tau_m$ is higher than a third-order effect compared with the decrement $\tau_t$. When the terms higher than the first-order are neglected, the increment $\tau_m$ can be ignored. Therefore, regarding the effects of the shear stress in the high frequency band region, it can be understood that the decrement effect is more predominant than the increment effect.

Here, if a change in the shear stress $\tau_W$ in a bubbly flow field is considered to be caused by the mixing length decrement $l_{mb}$ in the gas mixing length $l_m$ due to the presence of the bubble, the shear stress $\tau_W$ on the wall surface can be expressed by equation (20).

$$\tau_w = \left(\mu_m + \rho_L l_m^2 \frac{\partial \bar{u}_L}{\partial y}\right)\frac{\partial \bar{u}_L}{\partial y} \tag{20}$$

where $\mu_m$ is an apparent viscosity coefficient (a coefficient in molecular viscosity term).

Because the vortex viscosity element (Reynolds stress) in the second term is larger than the molecular viscosity element in the first term in the turbulent flow region, the shear stress $\tau_W$ on the wall surface can be expressed as in equation (21).

$$\tau_w = \rho_L l_m^2 \left(\frac{\partial \bar{u}_L}{\partial y}\right)^2 \tag{21}$$

$$= \rho_L(l_{m0}-l_{mb})^2\left(\frac{\partial \bar{u}_L}{\partial y}\right)^2$$

$$= \rho_L(l_{m0}^2 - 2l_{m0}l_{mb})\left(\frac{\partial \bar{u}_L}{\partial y}\right)^2$$

$$= \tau_{wo} - \tau_t$$

where $\tau_{WO}$ is the characteristics Reynolds stress for the liquid phase. Shear stress decrement $\tau_t$ caused by the differential velocity between gas/liquid phases is given by the following equation (22)

$$\tau_i = 2\rho_L l_{m0} l_{mb}\left(\frac{\partial \bar{u}_L}{\partial y}\right)^2 \tag{22}$$

Comparing equation (22) with equation (17), it can be seen that the mixing length change $l_{mb}$ is given by equation (23).

$$l_{mb} = \frac{81\kappa}{2\pi^2}\left(\frac{v_L T_{*L}}{d_b}\right)^2 \frac{\alpha_w}{l_{m0}} \tag{23}$$

$$= \frac{81\kappa}{2\pi^2}\left(\frac{v_L T_{*L}}{d_b}\right)^2 \frac{\alpha_w}{y}$$

Dimensionally, the product of integral time-scale $T_{*L}$ (time term) and the squared average of the turbulent velocity (length/time) expresses a ½ of the mean free path of the bubble (length term), and therefore, this quantity may be considered to be proportional to the gas mixing length $l_m$. Particularly, in a region obeying the logarithmic law, equation (24) can be established to lead to equation (25).

$$T_{*L} = (T_{*L}\hat{v}_L')(\hat{v}_L')^{-1} \propto l_m(\hat{v}_L')^{-1} = \left(\frac{\partial \bar{u}_L}{\partial y}\right)^{-1} = \frac{y}{U_\tau} \tag{24}$$

and $$v_L T_{*L} = b\left(\frac{v_L}{U_\tau}\right)y \tag{25}$$

where b is a constant of proportionality and the term inside the bracket $v_L/U_\tau$ relates to the length (wall variable) of the viscous bottom layer.

Substituting equation (25) in equation (23), the mixing length change $l_{mb}$ is expressed as in equation (26).

$$l_{mb} = \frac{81}{2\pi^2}\left(b \times \frac{v_L/U_\tau}{d_b}\right)^2 \alpha_w y \tag{26}$$

Grouping all the proportionality constants in equation (26) in an empirical constant $\alpha$ given by equation (28), equation (26) can be re-expressed as in equation (27).

$$l_{mb} = \left(\frac{v_L/U_\tau}{d_b/a}\right)^2 \alpha_w y \tag{27}$$

where $$a^2 = \frac{81}{2\pi^2}b^2 \tag{28}$$

It can be understood from equation (27) that the effects of a bubble can be expressed by revising the normal wall constant $\kappa$ for non-bubbly flow. Parametric variables are summarized in the following equations (29)–(32).

$$l_{m0} = \kappa y \quad (29)$$

$$l_{mb} = \kappa_2 y \quad (30)$$

$$l_m = l_{m0} - l_{mb} = (\kappa - \kappa_2)Y = \kappa_1 y \quad (31)$$

$$\kappa_1 = \kappa - \kappa_2 \quad (32)$$

Logarithmic law can still be applied, and these expressions are consistent with the premises of equation (25). In other words, a revised wall constant $\kappa_2$ for bubbly flow can be expressed as in equation (33).

$$\kappa_2 = \left(\frac{v_L/U_\tau}{d_b/a}\right)^2 \alpha_w \quad (33)$$

Therefore, the operative wall constant $\kappa_1$ for bubbly flow can be expressed by subtracting the revised wall constant $\kappa_2$ from the normal wall constant $\kappa$ for non-bubbly flow (i.e., single phase) according to equation (34).

$$\kappa_1 = \kappa - \kappa_2 \quad (34)$$

$$= \kappa - \left(\frac{v_L/U_\tau}{d_b/a}\right)^2 \alpha_w$$

Equation (34) has an extremely interesting structure. Control parameters for turbulent flow are contained inside the bracket, and are expressed by a ratio of the size of viscous sublayer and the size of the bubble (denominator $d_b/a$ is proportional to the bubble diameter). From equation (25), it can be seen that the extent of turbulent flow is deeply related to the extent of viscous sublayer, and therefore, the analytical model in the present embodiment suggests that the numerical simulation should be based on the ratio of bubble size and the extent of the turbulent flow field. Looking only at this result, the present model is not inconsistent with past experimental observations that turbulent control is achieved when the bubble size is small relative to the extent of turbulent flow field.

1.2 Low-frequency Band Region

In the low frequency band region, the shear stress decrement $\tau_t$ caused by the bubble, given in equation (17), is of the order of $(T\omega_L)^2$ and is very small. Therefore, the shear stress $\tau_W$ is given by adding the increment $\tau_m$ to the shear stress $\tau_{W0}$ for nonbubbly flow to yield an equation (35).

$$\tau_w = \tau_{wo} + \tau_m \quad (35)$$

$$= \tau_{wo} + \rho_L \frac{d_b \alpha_w \hat{v}'_L}{2\omega_L}\left(\frac{\partial \bar{u}_L}{\partial y}\right)^2$$

2. Frictional Resistance

An approximate solution in the high frequency band region, where a decrease in the shear stress plays the dominant role as explained above, can be represented by the skin-friction ratio $C_f/C_{f0}$, and a method of computing this ratio will be presented in the a following. Although the solution is approximate, it has an advantage that logarithmic solutions can avoid a need for complex function expressions. Subscript "0" refers to the non-bubbly flow field, that is, a single phase flow field.

In a flow field without a bubble whose velocity distribution is logarithmic, the following equations (36)–(39) can be established.

$$u_0^+ = \frac{1}{\kappa}\log y_0^+ + B \quad \text{where } B \text{ is a constant} \quad (36)$$

$$u_0^+ = \frac{u}{U_{\tau 0}} \quad (37)$$

$$y_0^+ = \frac{y}{\left(\frac{v}{U_{\tau 0}}\right)} \quad (38)$$

$$U_{\tau 0} = \sqrt{\frac{\tau_{wo}}{\rho}} \quad (39)$$

When a bubble is present, the following equations (40)–(43) can be established in correspondence to equations (36)–(39) by using the operative wall constant $\kappa_1$.

$$u^+ = \frac{1}{\kappa_1}\log y^+ + B \quad (40)$$

$$u^+ = \frac{u}{U_\tau} \quad (41)$$

$$y^+ = \frac{y}{\left(\frac{v_L}{U_\tau}\right)} \quad (42)$$

$$U_\tau = \sqrt{\frac{\tau_w}{\rho_L}} \quad (43)$$

The reason for assuming that B is constant in both flow fields, with or without the bubble on the wall, is based on the reported experimental observation (Iwashina Chiaki, Tokyo University, Faculty of Engineering, Marine Engineering Department, Graduate Thesis "Mechanisms for turbulent-friction reduction using micro-bubbles", 1998) that there is no change in the pattern of turbulent flow near the wall (log $y^+ \rightarrow 0$). It was interpreted that this phenomenon indicates that B is constant.

If the position variable y is assumed to be equal to the thickness $\delta$ of the turbulent boundary layer (turbulent boundary layer thickness $\delta$ is the same regardless of the presence or absence of the bubble), equations (36) and (40) above can be re-written as equations (44), (45).

$$\sqrt{\frac{2}{C_{f0}}} = \frac{1}{\kappa}\log \delta_0^+ + B \quad (44)$$

$$\sqrt{\frac{2}{C_f}} = \frac{1}{\kappa_1}\log \sqrt{\frac{C_f}{C_{f0}}} \delta_0^+ + B \quad (45)$$

In the meantime, local friction factor $C_{f0}$ in non-bubbly flow and the same in bubbly flow $C_f$ are expressed, respectively, by equations (46) and (47).

$$C_{f0} = \frac{\tau_{wo}}{\frac{1}{2}\rho U^2} \quad (46)$$

$$C_f = \frac{\tau_w}{\frac{1}{2}\rho_L U^2} = \frac{\tau_w}{\frac{1}{2}(1-\alpha_w)\rho U^2} \quad (47)$$

At this time, by subtracting equation (44) from equation (45), equation (48) is obtained.

$$\sqrt{\frac{2}{C_{f0}}}\sqrt{\frac{C_{f0}}{C_f}} - \sqrt{\frac{2}{C_{f0}}} = -\frac{1}{\kappa_1}\log_e\sqrt{\frac{C_{f0}}{C_f}} + \left(\frac{1}{\kappa_1} - \frac{1}{\kappa}\right)\log\delta_0^+ \quad (48)$$

The term $(C_f/C_{f0})^{1/2}$ in equation (48) is expanded about 1, and taking the first-order terms, the following equation (49) is obtained.

$$\sqrt{\frac{2}{C_{f0}}}\sqrt{\frac{C_{f0}}{C_f}} - \sqrt{\frac{2}{C_{f0}}} = \quad (49)$$

$$-\frac{1}{\kappa_1}\left(1 - \sqrt{\frac{C_{f0}}{C_f}}\right) + \left(\frac{1}{\kappa_1} - \frac{1}{\kappa}\right)\log\delta_0^+$$

Further, expanding the viscous sublayer term $v_L/U_\tau$ in the operative wall constant $\kappa_1$ for bubbly flow, the following equation (50) is obtained.

$$\frac{v_L}{U_\tau} = \frac{v_L}{U}\sqrt{\frac{2}{C_f}} = \sqrt{\frac{C_{f0}}{C_f}}\frac{v_L}{U}\sqrt{\frac{2}{C_{f0}}} \quad (50)$$

Equation (50) is substituted in equation (33) to obtain $\kappa_2$, which is substituted in equation (34) to obtain $\kappa_1$, and the $\kappa_1$ so obtained is substituted in equation (49) to solve for the skin-friction ratio $C_f/C_{f0}$ to produce the following equation (51).

$$\frac{C_f}{C_{f0}} = \left\{\frac{1 + \sqrt{2/C_{f0}}\,\kappa_{10} - 2(\log\delta_0^+)\kappa_{20}/\kappa}{1 + \sqrt{2/C_{f0}}\,\kappa_{10} - (\log\delta_0^+)\kappa_{20}/\kappa}\right\} \quad (51)$$

In equation (51), $\kappa_{10}$, $\kappa_{20}$, $\delta_0^+$ are respectively given by equations (52)–(54) given below. It is to be noted that bubbly flow of micro-bubbles is different from a suspension of dispersed fine particles in terms of the conditions related to the diameter of the bubble, and therefore, as a first zero-order approximation, it is assumed that $v_L=v$ where $v_L$ relates to the single liquid phase and $v$ relates to a two-phase mixture of liquid and bubble.

$$\kappa_{10} = \kappa - \kappa_{20} \quad (52)$$

$$\kappa_{20} = \left(\frac{v/U_{\tau0}}{d_b/a}\right)^2 \alpha_w \quad (53)$$

$$\delta_0^+ = \frac{\delta_0}{\left(\frac{v}{U_{\tau0}}\right)} \quad (54)$$

Further, in normalizing the shear force on the wall surface to a non-dimensional quantity with a common $\rho U^2/2$, the skin-friction ratio $C_f/C_{f0}$ given in equation (51) can be expressed as in equation (55).

$$\frac{C_f}{C_{f0}} = \left\{\frac{1 + \sqrt{2/C_{f0}}\,\kappa_{10} - 2(\log\delta_0^+)\kappa_{20}/\kappa}{1 + \sqrt{2/C_{f0}}\,\kappa_{10} - (\log\delta_0^+)\kappa_{20}/\kappa}\right\}(1 - \alpha_w) \quad (55)$$

3. Verification

Next, equation (55) was evaluated using a forty meter model ship (40-m model ship) to produce data that will be examined in detail below. The empirical constant a used in equation (27) was determined using the experimental data obtained by Guin et al. (1996).

The turbulent boundary layer in the stern-side of the 40-m model ship has a thickness of several hundred mm, which is sufficiently greater than the diameter of the bubbles of about 2 mm, and the float effect of the bubble is greater than the dispersion effect caused by turbulence. Therefore, the amount of bubbles congregating near the wall surface can be estimated roughly from the main fluid velocity and the air flow rate.

Near-wall void fraction of the 40-m model ship was considered as follows. The center velocity of a small-scale vortex generated by bubble ejection is assumed to be a half of the main fluid velocity, i.e., 0.5 U (refer to Kobayashi, 1983), and applying the $1/7$ multiplier rule, the position of the center of the small-scale vortex is about 0.1 $\delta$ from the surface of the wall. The end of the vortex is twice this value, i.e., 0.2$\delta$, and therefore, it may be considered that the region most relevant in generating turbulent flow stress is located between 0.1 $\delta$–0.2 $\delta$ from the wall surface.

Figure 3:
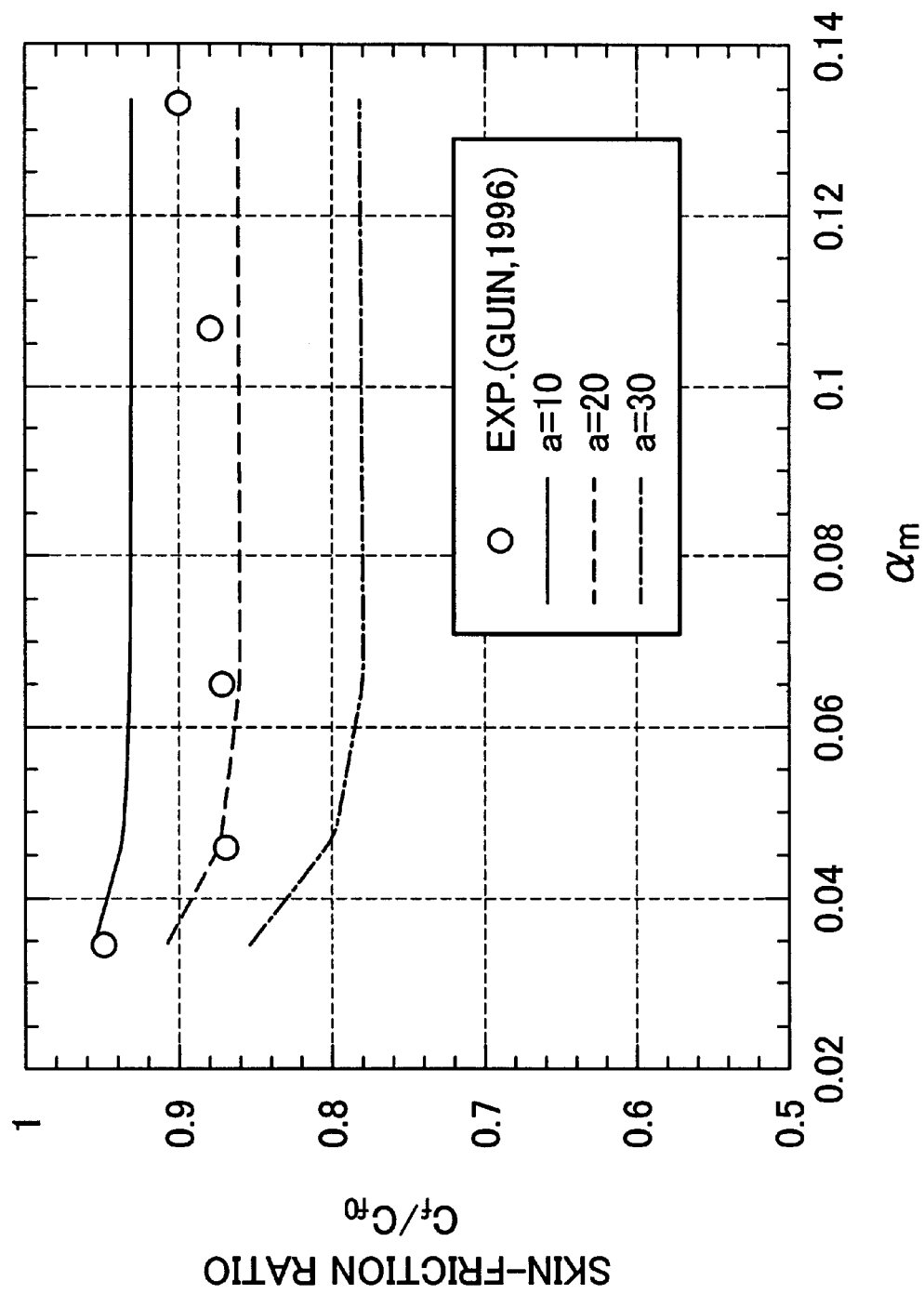
FIG. 3 is a graph showing a trend of a skin-friction ratio $C_f/C_{f0}$ to vary with average void fraction $\alpha_m$ for each frequency band in the first embodiment.
Figure 4:
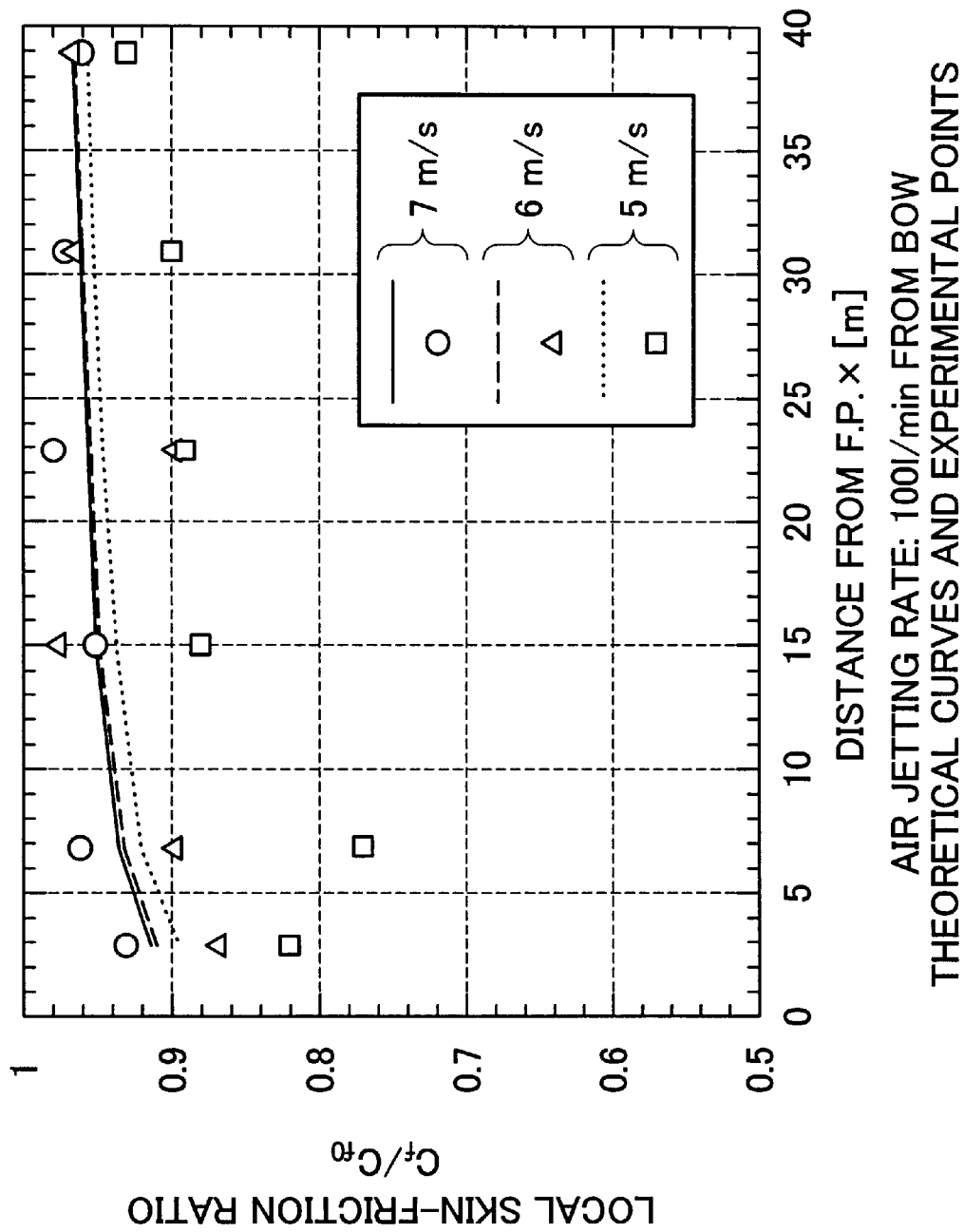
FIG. 4 is a graph showing the effects of adjusting the empirical constant a in the skin-friction ratio $C_f/C_{f0}$ in the first embodiment.

Based on such a consideration, the values of average void fraction $\alpha_W$ existing in the range between the wall surface and a depth of 0.2 $\delta$ were used in the analyses. Values of the parameters for non-bubbly flow were obtained using the $1/7$ multiplier rule, and the empirical constant a was chosen to be 20 so as to conform to the experimental data of Guin (1996) as shown in FIG. 3.

Figure 5:
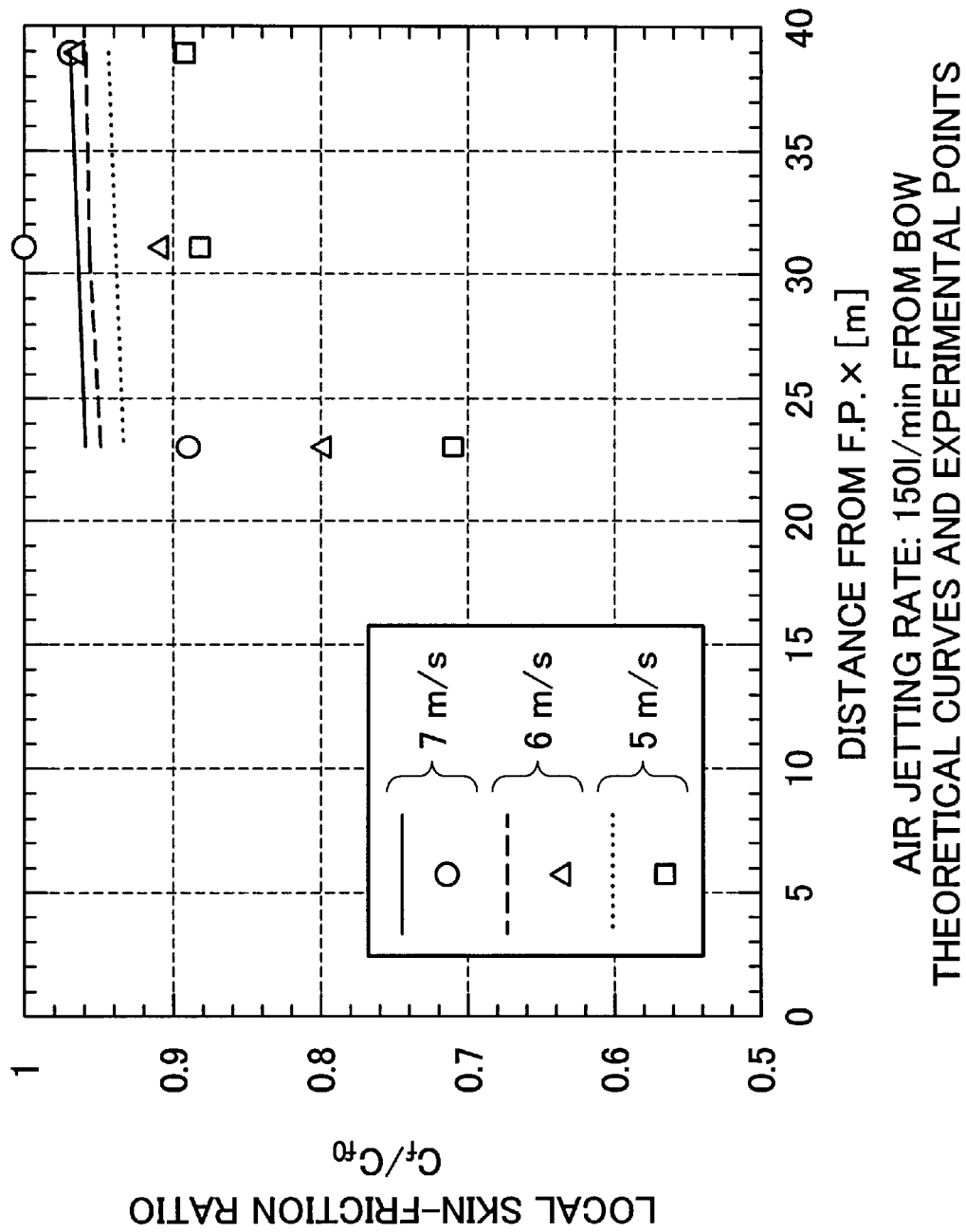
FIG. 5 is a first graph showing the verification results of the first embodiment.
Figure 6:
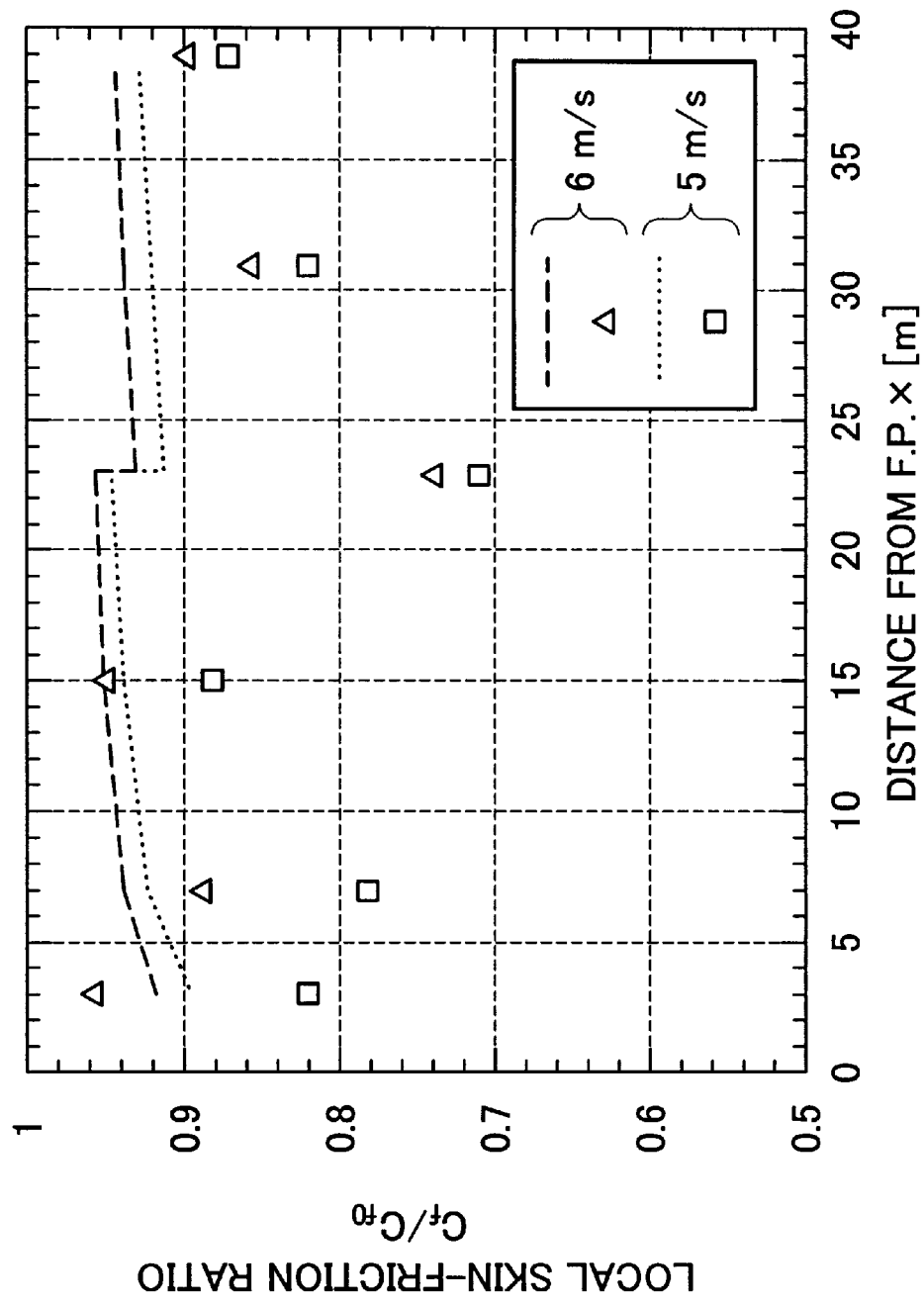
FIG. 6 is a second graph showing the verification results of the first embodiment.
Figure 7:
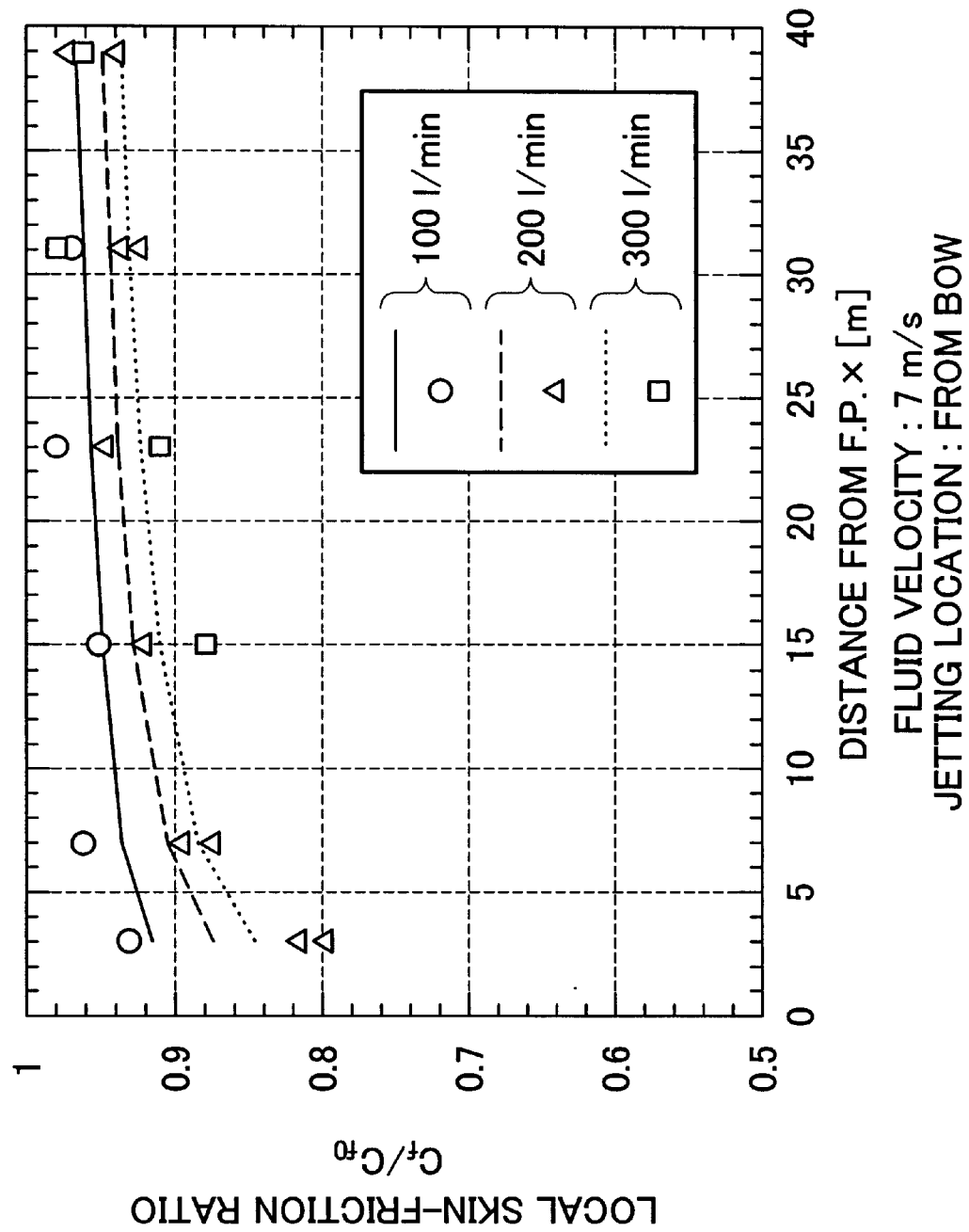
FIG. 7 is a third graph showing the verification results of the first embodiment.

Verification results are shown in FIGS. 4–7. Using the model ship velocity as a parameter, experimental results of skin-friction ratio $C_f/C_{f0}$ and theoretical results of $C_f/C_{f0}$ obtained from equation (55) are compared in FIG. 4, when the bubbles are a jetted from the bow of the model ship. Similarly, FIG. 5 compares the same when the bubbles are jetted from the center of the bottom surface. Similarly, FIG. 6 compares the same when the bubbles are jetted from the bow as well as from the center of the bottom surface. FIG. 7 compares the cases of using the flow rate of air ejected into water as a parameter, when the bubbles are jetted from the bow.

4. Conclusion

In this embodiment, equation (55) for evaluating the effects of skin-friction reduction was developed by re-examining more rigorously some of the variables which were not fully examined in the technique used in our previous work.

In deriving equation (55) by comparing the magnitudes of the time-constant of a bubble and the turbulence cycle in the turbulent boundary layer, three regions were identified: a low frequency band region where $T\omega_L \ll 1$, a middle frequency band region where $T\omega_L = O(1)$ and a high frequency band region where $T\omega_L \gg 1$. In this investigation, an approximate solution was developed for the high frequency band region. In the high frequency band region, it shows that, for a given value of [sublayer size]/[bubble size], skin-fiction ratio $C_f/C_{f0}$ produce a monotonic decrease to indicate that the bubbles exert a large influence.

Figure 8:
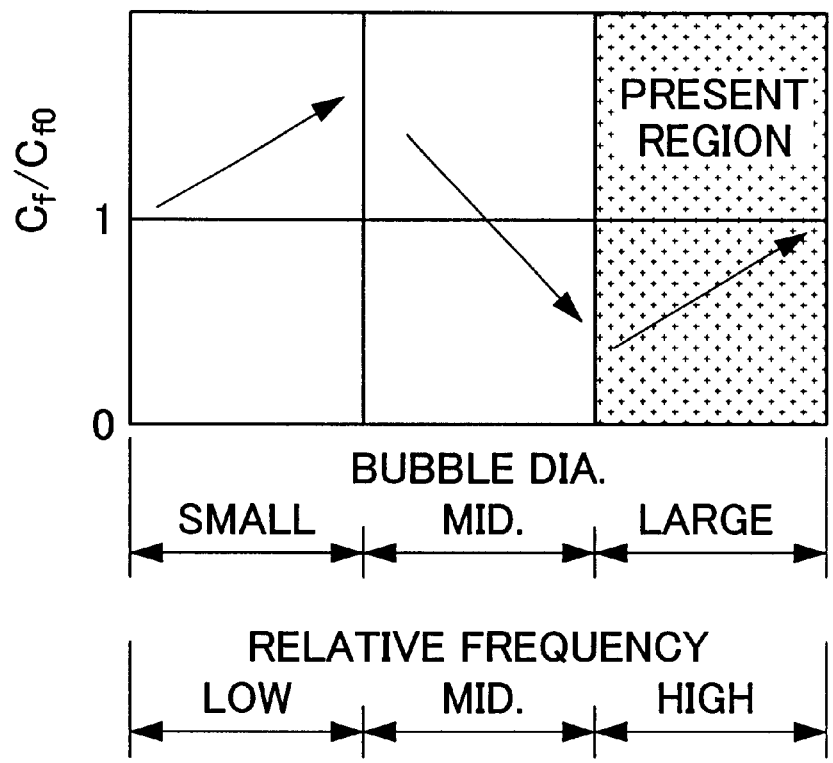
FIG. 8 is a fourth graph showing the results of verification of the first embodiment.

Also, in the high frequency band region, shear stress increment $\tau_m$ is small relative to the shear stress decrement $\tau_r$. However, in the middle frequency band region, the increment $\tau_m$ cannot be ignored and, contrastingly, in the low frequency band region, the effect of the shear stress increment becomes predominant. In other words, in the high frequency band region, response of the bubble movement is poor and the movement is small so that there is little kinetic mass exchange, and the effects of resistive force of the bubbles on the shear stress reduction become high. In contrast, in the low frequency band region, there is high activity in kinetic mass exchange, and the effect of shear stress increase becomes high. FIG. 8 shows a conceptual summary of the tendency of the skin-friction ratio, $C_f/C_{f0}$ in the three frequency regions.

As demonstrated in FIGS. 4–7, the analytical solution for $C_f/C_{f0}$ presented in this embodiment agrees qualitatively with experimental data. Especially, prediction on the bubbly flow retaining distance has been greatly increased. Also, it appears that the agreement is improved as the model ship speed is increased, and it is thought that this is caused by the fact that assumptions reflect the conditions in the high frequency band region. The future topics include development of analytical solutions for all frequency band regions and numerical computations.

Second Embodiment

Next, the second embodiment of the invention will be explained.

In the First Embodiment, the solution for the skin-friction ratio $C_f/C_{f0}$ was developed as in equation (55), by assuming that the operative wall constant $\kappa_1$ for bubbly flow was obtained by subtracting the revised wall constant $\kappa_2$ from the normal wall constant $\kappa$ for non-bubbly flow as in equation (34).

However, other parametric input terms, such as near-wall void fraction $\alpha_W$ and the bubble diameter $d_b$ were not examined in sufficient detail. There are various measured data on bubble diameters, and one aspect of the difficulty is to unilaterally decide the bubble size to be used in the analysis.

In the second embodiment, simultaneous equations involving equation (34) and a governing equation for void fraction were established so that the terms for bubble diameter $d_b$ and the empirical constant a can be eliminated such that, in the newly developed equation for skin-friction reduction, bubble size was replaced by void fraction as an input parameter.

In the following explanation, it was considered that a linear pattern of void fraction distribution is the most stable in order to satisfy the following stability conditions for solving the simultaneous equations:

A. the governing equation for void distribution does not diverge; and
  B. the sum of the kinetic energy of bubbly flow (with consideration for suppressing the turbulent flow) and potential float energy of bubbly flow should be minimized.

Within such a framework, two types of fluid flow effects on bubbly flow were considered: one-way coupling approach which considers fluid flow affecting the movement of bubbles; and two-way coupling approach which considers fluid flow effects on the bubble movement as well as bubble movement effects on the fluid flow.

1. Governing Equation for Void Fraction Distribution

Basic assumptions and methodology were adopted from a 43rd publication of the JSPC (Joint Ship Propulsion Committee, 1997), and the governing factors for dispersion of bubbles were attributed to turbulence and float force, for simplicity. It was considered that bubbly flow velocity was determined in all cases by resistive forces. In the Stokes equations, force is proportional to velocity so that it is not necessary to establish kinetic equations, for describing the movement of bubbles on the basis of interacting forces, and that total velocity can be expressed by superposition of velocity expressions for various driving factors. Bubbles are treated as dispersing particles forming a continuous string of particles, that is, behave as a gas phase.

Figure 9:
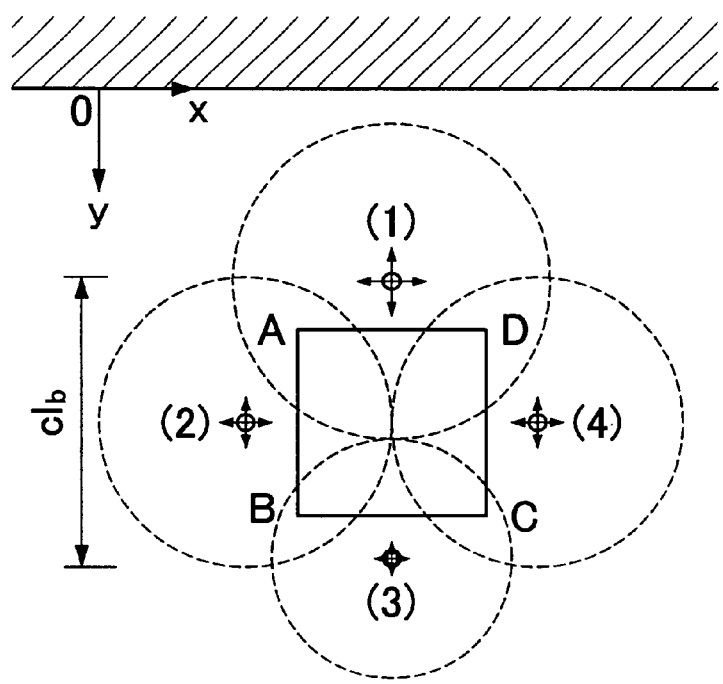
FIG. 9 a conceptual drawing of the turbulent flow model in the second embodiment.

FIG. 9 shows a model for analyzing the movement of bubbles. An examination region bounded by points A, B, C and D is designated within the turbulent boundary layer, and is surrounded by four dispersing particles (1)–(4). The center of each bubble represents the center of movement of each bubble, and the dotted line represents a circular boundary of free movement of each bubble, and each diameter representing a respective mean free path. The distance between the centers is assumed to be equal to the mean free path.

Here, a term equivalent to the mean free path in the two-dimensional theory of turbulent boundary layer is the mixing length, therefore, as a first-order approximation, the distance between the centers may be expressed as $cl_b$ in terms of the mixing length $l_b$ of the gas phase and an empirical constant c. Physically, the constant c relates to a dispersion coefficient. Also, the distance between the centers relates to a distance between the neighboring vortexes, and can be interpreted as a measure of the vortex length.

Designating and a flow flux in X-direction from boundary AB to boundary BD as $j_x$, the following and flow flux in y-direction from boundary AD to boundary CD as $j_y$, the following relation can be derived from the law of conservation of mass.

$$\frac{\partial j}{\partial x} + \frac{\partial j_y}{\partial y} = 0 \tag{56}$$

When a gas phase having a void fraction a disperses in the liquid phase, and travels while under the influence of a resistive force caused by the average fluid velocity and a float force, the flow fluxes $j_x$, $j_y$ can be approximated by the following expressions, respectively.

$$j_x = \alpha \bar{u}_L - \left[\left\{\alpha \hat{v}_b + \frac{cl_b}{2}\frac{\partial}{\partial x}(\alpha \hat{v}_b)\right\} - \left\{\alpha \hat{v}_b - \frac{cl_b}{2}\frac{\partial}{\partial x}(\alpha \hat{v}_b)\right\}\right] \tag{57}$$

$$= \alpha \bar{u}_L - cl_b \frac{\partial}{\partial x}(\alpha \hat{v}_b) \text{ and}$$

$$j_y = \alpha \hat{v}_L - \alpha q_g - cl_b \frac{\partial}{\partial y}(\alpha \hat{v}_b) \tag{58}$$

where $q_g$ is an ascending velocity of the bubble due to the float force and $v_b$ is a bubble velocity in y-direction.

The second term in equation (57) relates to a flow flux induced by the turbulent velocities of bubble (2) and bubble (4) shown in FIG. 9. Also, the third term in equation (58) relates to a flow flux induced by the turbulent velocities of bubble (1) and bubble (3).

At this time, premises indicated in equations (59)–(61) are selected. These conditions are set to zero, meaning that substitution of equations (57), (58) in equation (56) produce results which can be neglected in comparison with other terms. The order of magnitude was judged on the basis of the ⅐ multiplier rule. In these equations, Re stands for Reynolds number.

$$\hat{v}_L \approx 0 \tag{59}$$

$$\frac{\partial}{\partial x}(\alpha \bar{u}_L) = O\left(\frac{1}{Re^{11/10}}\right) \approx 0 \tag{60}$$

$$\frac{\partial}{\partial x}(\alpha \bar{v}_L) = O\left(\frac{1}{Re^{11/10}}\right) \approx 0 \tag{61}$$

Under these conditions, equations (57), (58) are substituted in equation (56) to obtain equation (62).

$$\frac{\partial}{\partial y}\left\{\alpha q_g + c l_b \frac{\partial}{\partial y}(\alpha \hat{v}_b)\right\} = 0 \quad (62)$$

Considering that the flow flux in y-direction is zero at the wall surface, the following equation (63) is established.

$$\alpha q_g + c l_b \frac{\partial}{\partial y}(\alpha \hat{v}_b) = 0 \quad (63)$$

Expanding equation (63) leads to equation (64). In this embodiment, equation (64) is designated as the governing equation for void fraction distribution.

$$c l_b^2 \left(\alpha \frac{\partial \bar{u}_L}{\partial y^2} + \frac{\partial \alpha}{\partial y}\frac{\partial \bar{u}_L}{\partial y}\right) + \alpha q_g = 0 \quad (64)$$

In equation (64), first and second terms relate to flow fluxes expressing dispersion caused by turbulence. Of the two, the first term is considered to be related to liquid-controlled dispersion caused by the liquid turbulence while the second term is considered to be related to void-controlled dispersion.

2. Mixing length of Gas Phase

To obtain a gas phase mixing length $l_b$, it is necessary to examine again the kinetic equation based on movement of the bubbles. In the near-wall region where the velocity distribution in a flow field obeys the logarithmic law, the relation between the gas phase mixing length $l_b$ and the actual (not apparent) liquid phase mixing length $l_{m0}$ is derived as shown in equations (65) and (66).

$$l_b = \hat{Y} = \frac{1}{T\omega_L^2}\hat{v}_L' \quad (65)$$
$$= \frac{36 v_L}{d_b^2 \omega_L^2} l_{m0} \frac{U_\tau}{\kappa_1 d_b/2}$$
$$= \frac{18}{\pi^2} \frac{v_L T_{*L}^2}{d_b^3} \frac{U_\tau}{\kappa_1} l_{m0}$$
$$= \frac{18}{\pi^2} \frac{b^2}{v_L d_b^3}\left(\frac{v_L}{U_\tau}y\right)^2 \frac{U_\tau}{\kappa_1} l_{m0}$$
$$= \frac{9 b^2}{2\pi^2 \kappa_1} \frac{v_L}{U_\tau d_b} l_{m0}$$

and $$\frac{l_b}{l_{m0}} = \frac{9 b^2}{2\pi^2 \kappa_1} \frac{v_L}{U_\tau d_b} \quad (66)$$

Where $U_t$ is frictional velocity. Also, the constant b satisfies equation (67) shown below and is related to the empirical constant a according to equation (68).

$$v_L T_{*L} = b\left(\frac{v_L}{U_\tau}\right)y \quad (67)$$

and $$\frac{9\sqrt{\kappa}}{\pi} b = a \quad (68)$$

3. Analytical Solution

Before obtaining an expression for void fraction distribution, liquid phase mixing length $l_{m0}$ is defined as follows, for convenience.

$$l_{m0} = \kappa y \sqrt{1-y/\delta} \quad (69)$$

In the region where the velocity distribution in a flow field obeys the logarithmic law, the equations (70) and (71) are established.

$$\frac{\partial \bar{u}_L}{\partial y} = \frac{1}{\kappa_1}\frac{U_\tau}{y} \quad (70)$$

$$\frac{\partial^2 \bar{u}_L}{\partial y^2} = \frac{1}{\kappa_1}\frac{U_\tau}{y^2} \quad (71)$$

Obtaining the gas phase mixing length $l_b$ from equations (66) and (69), and substituting the resulting $l_b$ together with equations (70), (71) in the governing equation (64) for void fraction, equation (72) is obtained.

$$y\left(1-\frac{y}{\delta}\right)\frac{\partial \alpha}{\partial y} = \left\{\left(1-\frac{y}{\delta}\right) - K_0\right\}\alpha \quad (72)$$

were $K_0$ is a constant.

In this case, if it is assumed that a local void fraction $\alpha$ is a function only of the position parameter y, equation (72) can be rewritten as follows.

$$y\left(1-\frac{y}{\delta}\right)\frac{d\alpha}{dy} = \left\{\left(1-\frac{y}{\delta}\right) - K_0\right\}\alpha \quad (73)$$

Equation (73) is a separable-variable differential equation, and a solution can be derived readily as follows.

$$\alpha = K_i y^{-K_0+1}\left(1-\frac{y}{\delta}\right)^{K_0} \quad (74)$$

where the constants $K_0$ and $K_1$ are given by equations (75) and (76), given respectively below, where $\alpha_{av}$ in equation (76) is an average void fraction in the turbulent boundary layer.

$$K_0 = \frac{9\kappa_1^3 U_\tau g}{2 c v_L^3}\left(\frac{d_b}{a}\right)^4 \quad \text{and} \quad (75)$$

$$K_1 = \frac{\alpha_{av}(\delta - d_b/2)}{\int_{d_b/2}^{\delta}\left\{y^{-K_0+1}\left(1-\frac{y}{\delta}\right)^{K_0}\right\}\delta y} \quad (76)$$

These constants $K_0$ and $K_1$ are parameters for determining the void fraction distribution, where $K_0$ specifies the peak position and $K_1$ specifies the overall size of the void fraction.

Figure 10:
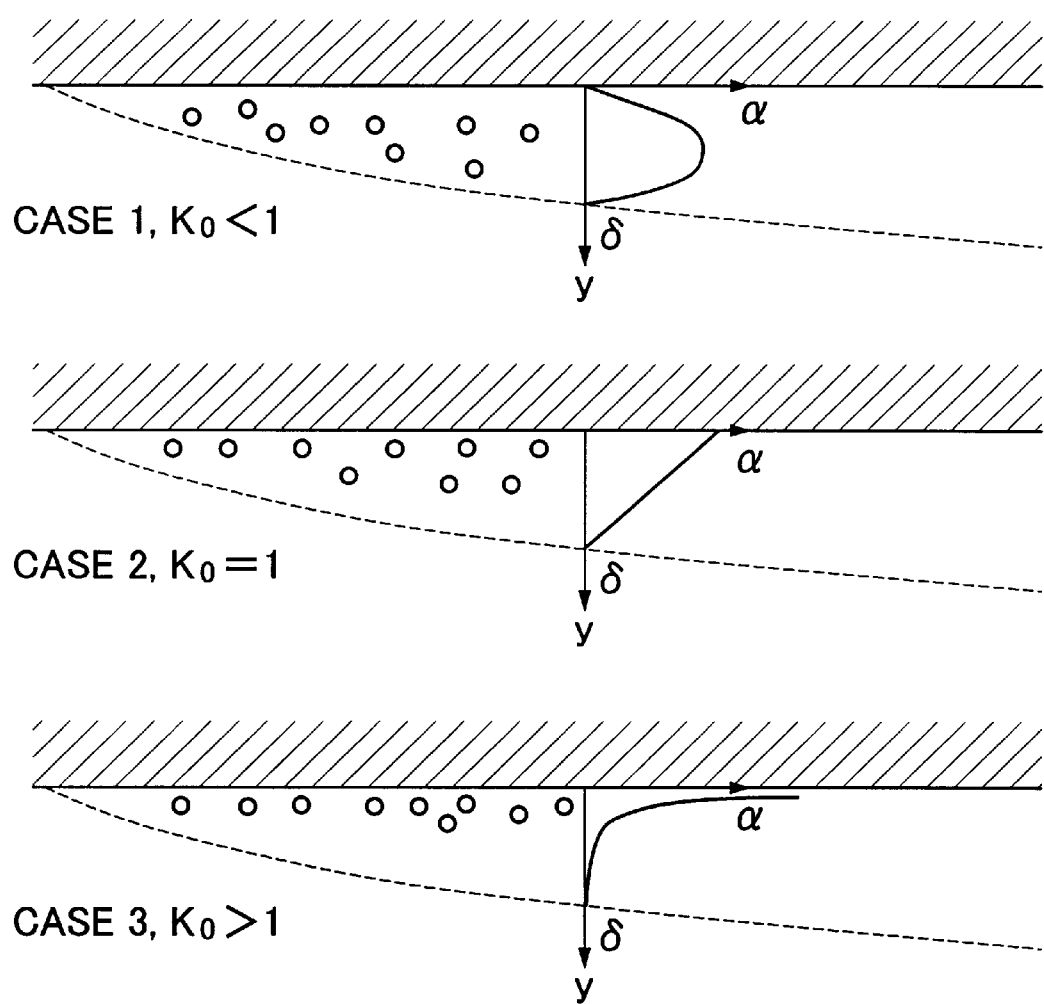
FIG. 10 is a schematic drawing to show the variation in the pattern of void fraction distribution in the second embodiment.

FIG. 10 is a graph showing how the local void fraction $\alpha$ in y-direction varies when the constant $K_0$ is altered. Case 1 illustrates a local void distribution when $K_0<1$; Case 2 when $K_0=1$; and Case 3 when $K_0>1$.

In Case 1, the local void fraction $\alpha$ diverges at the wall surface (y=0). In Case 2, divergence does not occur, and the local void fraction $\alpha$ is maximum at the hull surface. In Case 2, due to changes in the operative wall constant $\kappa_1$, the turbulence appears to be most suppressed and the kinetic energy is minimized, and comparing with Case 3, float potential energy is minimized. Therefore, it can be considered that Case 2 represents the most stable void fraction distribution.

As shown by equation (75), the parameter $K_0$ varies as the 4th power of the bubble diameter, so that the local void fraction $\alpha$ is very sensitive to changes in the bubble dimension. Considering that the empirical constant a also exerts a large influence on the parameter $K_0$, it is extremely difficult to unilaterally select a bubble size, which varies widely in reality, and to input some bubble diameter $d_b$ as a variable to estimate the void fraction distribution.

For these reasons, the approach taken in this embodiment is to adjust the parameters $K_0$, $K_1$ in the void fraction distribution equation (74) until the computed α matches with the actual void fraction distribution, and the value of $K_0$ so obtained is used in equation (75) to derive a value of $(d_b/a)$. Simultaneous equations are then established with equation (34) to develop an expression for skin-friction ratio $C_f/C_{f0}$ by two-way coupling approach.

Also, in equation (75), an expression for one-way coupling can be conveniently developed by replacing the bubbly flow frictional velocity $U_\tau$ with the non-bubbly flow $U_{\tau 0}$, and replacing the constant $\kappa_1$ for bubbly flow with $\kappa$ for non-bubbly flow.

Figure 11:
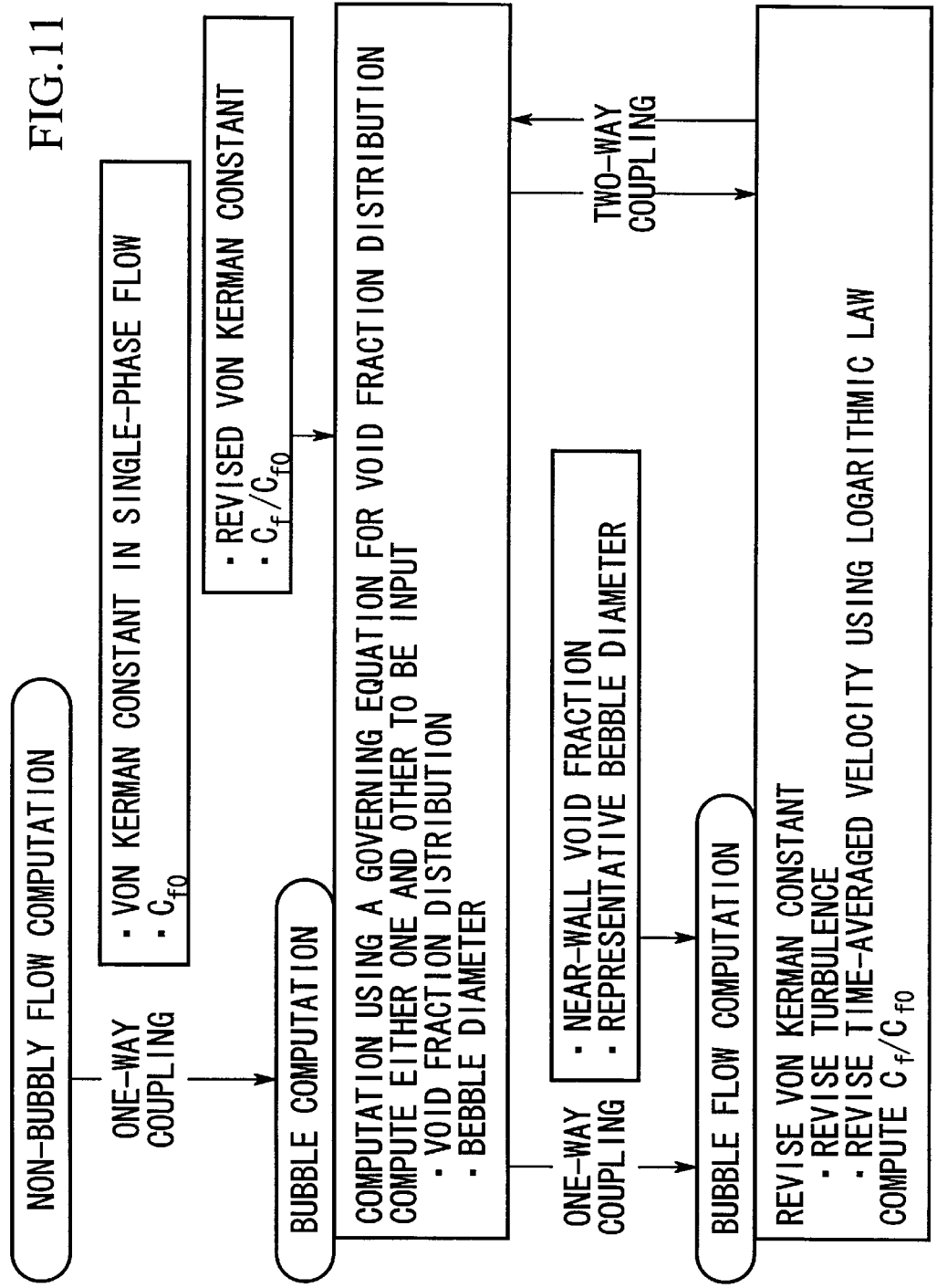
FIG. 11 is a flowchart to show the steps for computing the skin-friction ratio $C_f/C_{f0}$ in the second embodiment.

FIG. 11 is block diagram of the computational steps for one-way coupling and two-way coupling approaches. These expressions, one-way coupling and two-way coupling, are used in describing Lagrangian models, but they are useful also in describing the present computational models. One-way coupling approach is a method to perform computations related to bubbly fluid flow based on computed results related to bubbles, and two-way coupling approach is a method to perform computations related to bubbly fluid flow based on computed results related to bubbles, and feed back the results related to bubbly fluid flow to perform computations related to bubbles.

4. Verification 4.1 Two-dimensional Channel

In this section, the aspects of the model examined are determination of empirical constant c, evaluation of the method for approximation and the qualitative expressive ability of the model.

Figure 12:
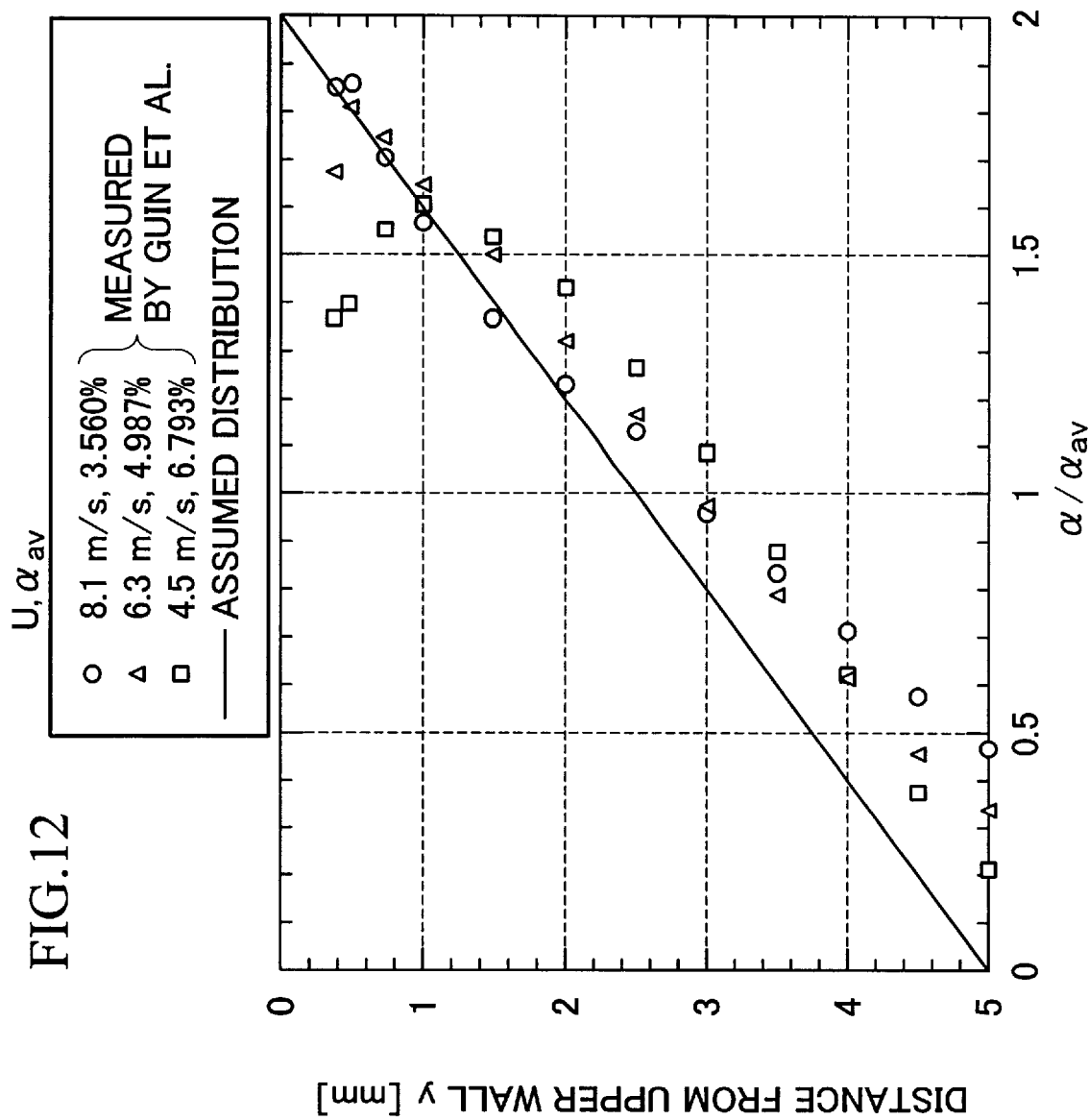
FIG. 12 is a graph showing the verification results of void fraction distribution in the second embodiment.

Examination of the experimental results (refer to Guin et al. 1996) for a two-dimensional channel (plate on top) reveals that the void fraction is close to zero in the middle of the channel and increases towards the wall in a linear manner (refer to FIG. 12), when the fluid flow velocity is close to practical ship speed, U=5~8 m/s, and the void fraction is less than 7%. Such a void distribution pattern is similar to Case 2 mentioned above. If the estimation precision can be maintained by limiting the distribution pattern to Case 2, it would be useful in practical situations even though the applicability range may be narrowed.

Therefore, examination process was carried out not only for two-way coupling approach and computations using near-wall void fraction data, but also for the case of convenient approximation based on one-way coupling approach and an assumption of linear distribution of void fraction (Case 2: $K_0$=1). As described later, trial computations were performed using the two-dimensional experimental data of Guin et al. on a 40-m model ship. Also, similar to the first embodiment, near-wall void fraction $\alpha_W$ was assumed to be the average void fraction existing within the distant of 0.2 δ from the wall surface.

Figure 13:
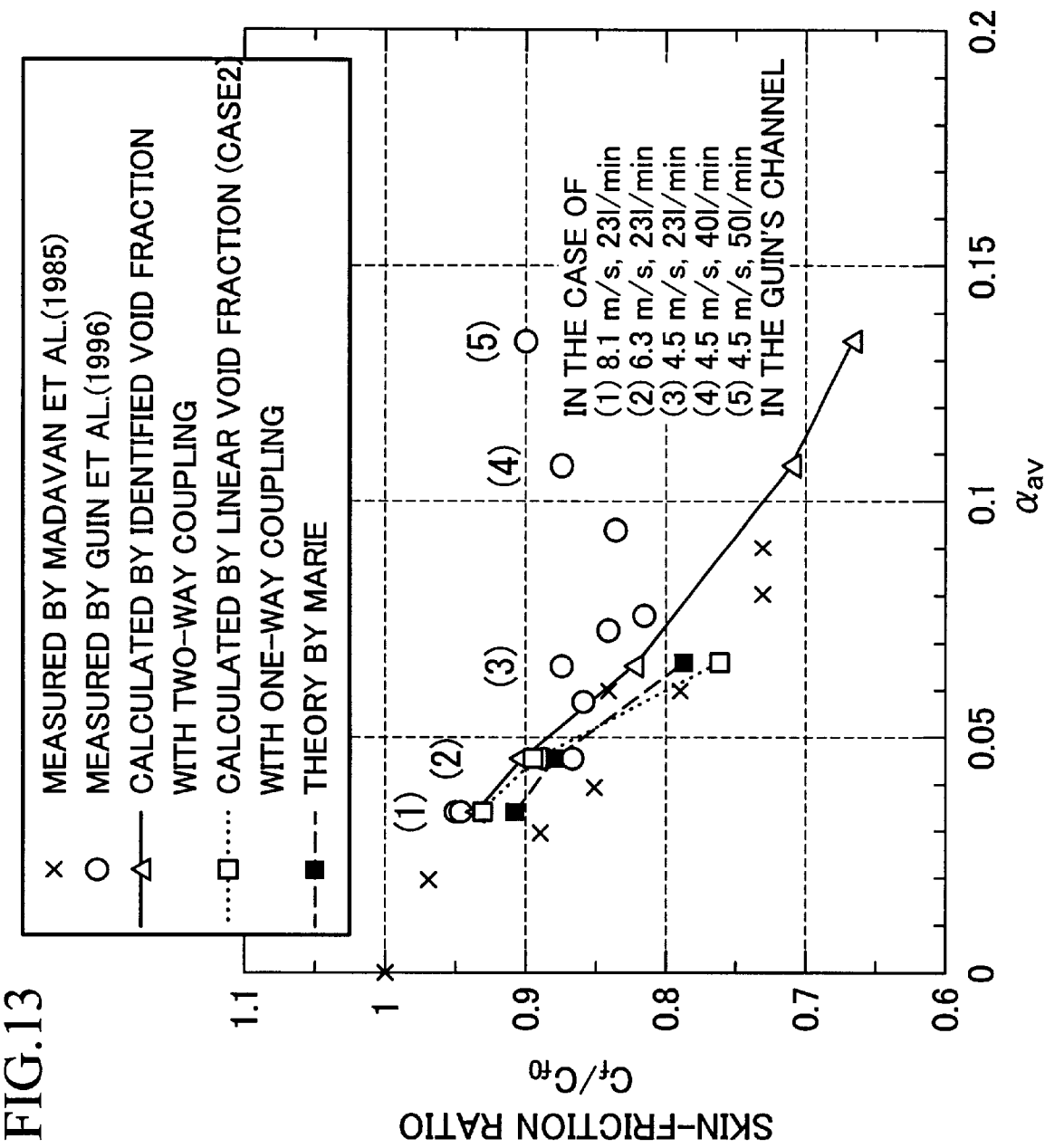
FIG. 13 a graph showing the verification results of void fraction distribution in a two-dimensional channel in the second embodiment.

FIG. 13 shows the results in the terms of the affects of average void fraction $\alpha_m$ (based on the total width of the channel) on the skin-fraction ratio $C_f/C_{f0}$ encountered in the fluid flowing within the channel. Equation (75), (76) were used to obtain void fractions which would duplicate the near-wall void fraction measured by Guin et al. The computed results using the two-way coupling approach (triangles) and those obtained using the one-way coupling approach (squares) are also shown in FIG. 13. For reference purposes, results obtained by Madavan (1984) are also plotted in FIG. 13.

In the two-way coupling approach, measured values of void fraction were input for the purpose of verifying the properties particular to the shear stress model. The trend seems to agree qualitatively in general. However, when the average void fraction $\alpha_m$ begins to exceed 0.05, significant quantitative difference begins to be observed. This is considered to be caused primarily by the fact that the skin-friction ratio $C_f/C_{f0}$ obtained by Guin et al. is normalized by the main fluid velocity in non-bubbly flow $U_{m0}$ while, for convenience, the present values of $C_f$ are normalized by the main fluid velocity in bubbly flow and those for $C_{f0}$ are normalized by the main fluid velocity in non-bubbly flow, and therefore, the results do not agree quantitatively, particularly when the flow path is narrow.

For the case of narrow flow path, it remains as a topic of future study to estimate the main fluid velocity for bubbly flow accurately by computation. It should be noted that the water tank used by Madavan, measuring 508×714 mm in cross section, is relatively large so that the influence of using a different normalization standard is relatively small. Also, the wall-surface void fraction is based on measured absolute values so that if there is an error in the absolute value of void fraction, computation results are affected directly by the magnitude of the error.

In the one-way coupling approach, the purpose is to examine the extent of applicability of the convenient methodology. Agreement is observed up to about 0.05 in the average void fraction $\alpha_m$. In the experiments using the 40-m model ship described later, maximum value of average void fraction $\alpha_m$ is obtained when the fluid velocity is 7 m/s, air jet flow rate is 300 l/min ejected at a distance x=3 m, which is the location of the sensor closest to the bow of the ship. Average void fraction observed under these conditions was 0.06 (relative to the thickness of the boundary layer).

Overall, average void fraction is much lower, and it is considered that the accuracy of estimation can be maintained even with the simplified approach of one-way coupling method. In this case, the near-wall void fraction $\alpha_W$ can be obtained using turbulent layer average void fraction $\alpha_{av}$ according to equation (77).

$$\alpha_W = 2\alpha_{av} \quad (77)$$

Empirical constant c was assumed to be 0.01. All subsequent computations are based on this value.

4.2 Experiments using the 40-m Model Ship

Computations for the 40-m model ship were performed by one-way coupling approach according to Case 2 in which the void fraction distribution is assumed to vary linearly.

Figure 14:
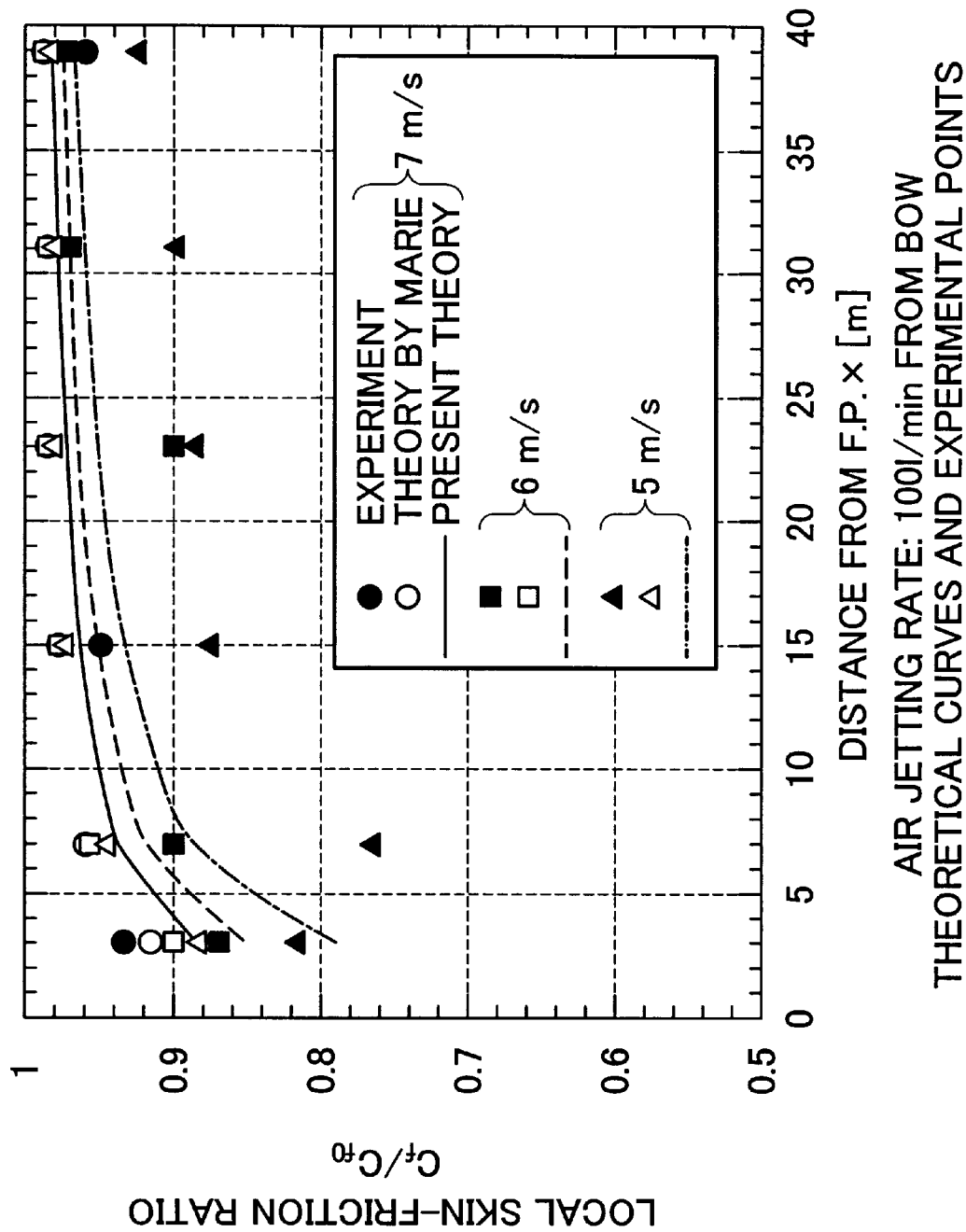
FIG. 14 is a first graph showing the results of verification of the second embodiment.

FIGS. 14~17 are graphs showing computed and measured results. FIG. 14 shows the effects of the distance from the origin of bubble jet on the skin-friction ratio $C_f/C_{f0}$ for various ship speed values, when the bubbles are ejected from the nozzles on the bow-bottom of the ship. FIG. 15 shows the same when the bubbles are ejected from the nozzles in the middle of the ship. FIG. 16 shows the same when the bubbles are ejected from the nozzles at both the bow and the middle of the ship. FIG. 17 shows the effects of the distance from the origin of the bubble jet on the skin-friction ratio $C_f/C_{f0}$ for various flow rates of gas jetting from the nozzles in the bow of the ship.

From FIG. 14, it can be seen that quantitative agreement between computation and observation is better at a fluid velocity of 5 m/s than at 7 m/s. This may be because the assumption of high frequency band is not appropriate for the flow fields in the range of 5~6 m/s. Analysis of frequency effects remains as a future topic.

The reason for the disagreement when the bubbles are ejected from the middle the ship may be because, immediately after ejection, near-wall void fraction increases temporarily due to the initial kinetic influence of the bubbles. The agreement improves towards downstream because the kinetic influence becomes less as the bubbles travel in the turbulent layer. FIG. 17 indicates that the effects of jet gas flow rate is well represented by the analytical model.

5. Conclusions (1) By solving simultaneous equations of a turbulent flow model and a governing equation for void fraction distribution, a methodology has been developed for computing a skin-friction ratio $C_f/C_{f0}$ by inputting a void fraction distribution pattern instead of the bubble diameter $d_b$. Also, the empirical constant a is eliminated in the process of solving the simultaneous equations.

(2) It was found that the quantitative expressions for approximation solution in the high frequency band region (turbulent flow model), with consideration for void fraction distribution, produced excellent results.

(3) Although the range of applicability becomes limited, estimation is possible even if a linear pattern is adopted for the void fraction distribution. When the main fluid velocity is in the range of 5~8 m/s and the average void fraction in the turbulent layer $\alpha_{av}$ is less than 0.05, the trend of skin-friction reduction can be estimated even if the void fraction distribution is approximated to be linear. In this case, estimation accuracy is maintained even with the one-way coupling approach.

Assumption of linearity of void fraction distribution pattern at low fluid velocity and low jet volume was made on the basis of experimental observations, and theoretically, this condition was achieved by providing stability conditions of non-divergence and energy minimization. Detailed mechanistic interpretation remains as a future topic, however.

Other reasons for disagreement may exist also. For example, there is possibility that, when external perturbation due to turbulent flow is small and the volumetric force is acting towards the interior of the ship, a stability condition may mean that the closer the bubble is to the wall the larger the bubble volume. It may also be that an apparent viscosity of the fluid changes as a result of mixing with the bubbles so that bubbly flow may be a phenomenon similar to spreading of an adhered high-viscosity fluid mass over the ship wall surface. Or, bubbly flow dynamics involves an ever-changing process of mixing of bubbles of various sizes in search of transient stability by collapsing and coalescing, leading to macroscopic adjustments in bubble sizes to achieve an ultimate dynamic equilibrium between void dispersion force and float force.

However, theoretically, void fraction distribution pattern is dependent on the 4th power of bubble diameter, so that macroscopic adjustment in bubble size occurs at a very small scale. At this stage of the model development, further discussion of microscopic analysis of bubbly fields comprised of various sizes of bubbles would be fruitless, and it remains as a large future topic.

Salient features of the method of the present invention are summarized in the following.

(1) In a high frequency band region, the method enables more accurate analysis of the effects of bubbly flow in reducing the skin-friction.

(2) The method enables to eliminate the bubble size $d_b$ from the operative wall constant $\kappa_1$ in the wall law for bubbly flow, by using actual void fraction distribution to develop a governing equation for void fraction distribution. Because $d_b$ is difficult to determine unilaterally from various experimental results and $d_b$ has such a large effect on any analytical solution for the skin-friction ratio $C_f/C_{f0}$, eliminating the bubble size as an input parameter contributes significantly to the ability of the model to estimate the skin-friction ratio $C_f/C_{f0}$ accurately.

(3) According to conventional theoretical approaches, friction reduction effects can be analyzed only for a plate configuration (bottom hull), but the development of equations in the direction at right angles to the ship surface (normal direction) enables the effects of bubbles acting on a slanted hull surface to be analyzed.

What is claimed is:

1. A method for analyzing effects of generating bubble jets in a flow field near a ship surface on reducing skin-friction in a cruising ship comprising the steps of:

obtaining a shear stress decrement $\tau_t$, produced by having a bubble in said flow field in terms of a resistive force $\Delta R_y$ acting on said bubble, derived from movements of said bubble, in a fluid flow direction, x-direction, along said cruising ship as well as in a direction at right angles to a ship wall surface, y-direction, in accordance with a definition of a high frequency band region in which a product of a bubble time-constant T and a turbulence frequency $\omega_L$ in said flow field is greater than 1;

obtaining an operative wall constant $\kappa_1$ in the wall law when there is a bubble having a parametric bubble diameter $d_b$, by assuming that said shear stress decrement is generated by a decrease in a mixing length; and obtaining a solution for skin-friction ratio, $C_f/C_{f0}$ in said high frequency band region, according to an expression relating said operative wall constant $\kappa_1$ to a local friction factor $C_f$ for bubbly flow, and an expression relating a normal wall constant $\kappa$ in the wall law in non-bubbly flow to a local friction factor $C_{f0}$ in non-bubbly flow.

2. A method according to claim 1, wherein said bubble diameter $d_b$ is eliminated as a parameter from said operative wall constant $\kappa_1$ in said wall law for bubbly flow, by specifying a governing equation for a void fraction distribution using an actual pattern of bubble distribution.

3. A method according to claim 2, wherein said governing equation for void fraction distribution is specified under stability conditions: to produce non-divergence in said governing equation; and to minimize a sum of the kinetic energy of bubbly flow, with consideration for suppressing the turbulent flow, and a potential float energy of bubbly flow.

4. A method for analyzing effects of generating bubble jets in a flow field near a ship surface on reducing skin-friction in a cruising ship comprising the steps of:

performing a Fourier transform on kinetic equations (1) and (2) for a bubble moving in x- and y-directions, representing a fluid flow direction and a direction at right angles to said ship surface, respectively, in terms of an added mass of a bubble $m_A$, a bubble diameter $d_b$, a dynamic liquid viscosity coefficient $v_L$, and obtaining an expression for a gain in x-direction $G_x$ and an expression for a gain in y-direction $G_y$ comprised of a bubble time-constant T and a turbulence frequency $\omega_L$, based on equations (3) and (4) respectively;

obtaining from equation (16) a resistive force $\Delta R_y$ acting on a bubble in a high frequency band region where a product of a bubble time-constant T and a turbulence frequency $\omega_L$ is greater than 1, in terms of a normal wall constant $\kappa$ in the wall law in non-bubbly flow, a fluid density $\rho_L$, a dynamic fluid viscosity coefficient $v_L$, and a time-averaged velocity in x-direction $u_L$, by assuming that a turbulence cycle $2\pi/\omega_L$ in said flow field is equal to said integral time-scale $T_{*L}$;

obtaining a shear stress decrement $\tau_t$ caused by said resistive force $\Delta R_v$ from equation (17);

obtaining a mixing length decrement $l_{mb}$ from equation (27) in terms of an empirical constant a, said bubble diameter $d_b$, said dynamic viscosity coefficient $v_L$, a frictional velocity $U_t$ and a near-wall local void fraction $\alpha_W$, by comparing said equation (17) with equation (22) which expresses a shear stress decrement r, that is assumed to be produced by a mixing length decrement $l_{mb}$;

obtaining a revising wall constant $\kappa_2$ in the wall law as in equation (33) by using said equation (27), and obtaining an expression as in equation (34) for an operative wall constants $\kappa_1$ for bubbly flow, in terms of said empirical constant a and said bubble diameter $d_b$ as parameters, by subtracting said revised wall constants $\kappa_2$ from said normal wall constant $\kappa$;

deriving equation (44) relating said normal wall constant $\kappa$ to a local friction factor $C_{f0}$ in non-bubbly flow, and equation (45) relating said operative wall constant $\kappa_1$ to a local friction factor $C_f$ in bubbly flow, according to equation (36) for non-bubbly flow velocity and equation (40) for bubbly flow velocity, assuming that a fluid velocity distribution obeys a logarithmic law and that a position parameter y is represented by a turbulent boundary layer thickness $\delta$;

subtracting said equation (44) from said equation (45) to obtain equation (48), and expanding a series expression $(C_f/C_{f0})^{1/2}$ in equation (48) about 1 so as to derive equation (49) comprised of first-order expansion terms while also expanding a bottom-layer term $v_L/U_t$ in said equation (48) for an operative wall constants $\kappa_1$ for bubbly flow, thereby deriving equation (50); and obtaining an analytical solution (55) for a skin-friction ratio $C_f/C_{f0}$ in said high frequency band region by substituting said equation (50) in said equation (33) to yield a first result and substituting said first result into said equation (34) to yield a second result and substituting said second result into said equation (49) and solving to obtain an expression for said analytical solution;

wherein equations referenced above are listed as follows;

$$\frac{m_A}{3\pi\mu_L d_b}\ddot{X} + \dot{X} = u'_L \tag{1}$$

$$\frac{m_A}{3\pi\mu_L d_b}\ddot{Y} + \dot{Y} = v'_L \tag{2}$$

$$\frac{\hat{\dot{X}}}{\hat{u}'_L} = \frac{1}{\sqrt{1+T^2\omega_L^2}} = G_X \tag{3}$$

$$\frac{\hat{Y}}{\hat{v}'_L} = \frac{1}{\sqrt{1+T^2\omega_L^2}}\frac{1}{\omega_L} = G_Y \tag{4}$$

$$\Delta\hat{R}_v = \frac{27}{4\pi}\kappa\rho_L(\varepsilon_L T_{*L})^2\left(\frac{\partial \bar{u}_L}{\partial y}\right)^2 \tag{16}$$

$$\tau_t = \frac{81}{\pi^2}\kappa\rho_L\left(\frac{v_L T_{*L}}{d_b}\right)^2\alpha_w\left(\frac{\partial \bar{u}_L}{\partial y}\right)^2 \tag{17}$$

$$\tau_t = 2\rho_L l_{mo} l_{mb}\left(\frac{\partial \bar{u}_L}{\partial y}\right)^2 \tag{22}$$

$$l_{mb} = \left(\frac{v_L/U_\tau}{d_b/a}\right)^2 \alpha_w y \tag{27}$$

$$\kappa_2 = \left(\frac{v_L/U_\tau}{d_b/a}\right)^2 \alpha_w \tag{33}$$

$$\kappa_1 = \kappa - \kappa_2 \tag{34}$$
$$= \kappa - \left(\frac{v_L/U_\tau}{d_b/a}\right)^2 \alpha_w$$

$$u_0^+ = \frac{1}{\kappa}\log y_0^+ + B \quad \text{where } B \text{ is a constant} \tag{36}$$

$$u^+ = \frac{1}{\kappa_1}\log y^+ + B \tag{40}$$

$$\sqrt{\frac{2}{C_{f0}}} = \frac{1}{\kappa}\log \delta_0^+ + B \tag{44}$$

$$\sqrt{\frac{2}{C_f}} = \frac{1}{\kappa_1}\log\sqrt{\frac{C_f}{C_{f0}}}\delta_0^+ + B \tag{45}$$

-continued $$\sqrt{\frac{2}{C_{f0}}}\sqrt{\frac{C_{f0}}{C_f}} - \sqrt{\frac{2}{C_{f0}}} = -\frac{1}{\kappa_1}\log\sqrt{\frac{C_{f0}}{C_f}} + \left(\frac{1}{\kappa_1} - \frac{1}{\kappa}\right)\log\delta_0^+ \quad (48)$$

$$\sqrt{\frac{2}{C_{f0}}}\sqrt{\frac{C_{f0}}{C_f}} - \sqrt{\frac{2}{C_{f0}}} = -\frac{1}{\kappa_1}\left(1 - \sqrt{\frac{C_{f0}}{C_f}}\right) + \left(\frac{1}{\kappa_1} - \frac{1}{\kappa}\right)\log\delta_0^+ \quad (49)$$

$$\frac{v_L}{U_\tau} = \frac{v_L}{U}\sqrt{\frac{2}{C_f}} = \sqrt{\frac{C_{f0}}{C_f}}\frac{v_L}{U}\sqrt{\frac{2}{C_{f0}}} \quad (50)$$

$$\frac{C_f}{C_{f0}} = \left\{\frac{1 + \sqrt{2/C_{f0}}\,\kappa_{10} - 2(\log\delta_0^+)\kappa_{20}/\kappa}{1 + \sqrt{2/C_{f0}}\,\kappa_{10} - (\log\delta_0^+)\kappa_{20}/\kappa}\right\}(1 - \alpha_w). \quad (55)$$

5. A method according to claim 4, wherein said bubble is considered to obey a law of conservation of mass expressed in equation (56) while moving in a flow field near said ship surface that includes a fluid flow flux $j_x$ in a fluid flow direction, x-direction, and a fluid flow flux $j_y$ at right angles to said ship surface, y-direction, as a result of dispersion of a gas phase having a local void fraction a, under an influence of a resistive force acting on said bubble caused by an average fluid velocity and a float force of said bubble;

approximating said $j_x$ in terms of a local void fraction α, an average fluid velocity in x-direction $u_L$, a squared average value of gas phase velocity in y-direction $v_b$, an empirical constant c, a gas phase mixing length $l_b$ as in equation (57), and approximating said $j_y$ in terms of said local void fraction α, an average fluid velocity in y-direction $v_L$, a bubble ascending velocity $q_g$, said empirical constant c, said gas phase mixing length $l_b$ as in equation (58) so as to derive an expression for a governing equation for a void fraction distribution as in equation (64);

solving said governing equation (64) to obtain an expression (74) for said local void fraction α in terms of parametric constants $K_0$, and $K_1$ and turbulent layer thickness δ;

determining a value for $K_0$ from an experimentally-obtained void fraction distribution pattern, and substituting said value of $K_0$ in an expression for $K_0$ in equation (75) to form simultaneous equations with said equation (34), thereby replacing said operative wall constant $\kappa_1$ for bubbly flow with a bubble diameter $d_b$ and an empirical constant a, and deriving an analytical expression for skin-fraction ratio $C_f/C_{f0}$ based on a void fraction distribution as a parameter, wherein equations reference above listed below.

$$\frac{\partial j_x}{\partial x} + \frac{\partial j_x}{\partial y} = 0 \quad (56)$$

$$j_x = \alpha\bar{u}_L - \left[\left\{\alpha\hat{v}_b + \frac{cl_b}{2}\frac{\partial}{\partial x}(\alpha\hat{v}_b)\right\} - \left\{\alpha\hat{v}_b - \frac{cl_b}{2}\frac{\partial}{\partial x}(\alpha\hat{v}_b)\right\}\right] \quad (57)$$
$$= \alpha\bar{u}_L - cl_b\frac{\partial}{\partial x}(\alpha\hat{v}_b)$$

$$j_y = \alpha\hat{v}_L - \alpha q_g - cl_b\frac{\partial}{\partial y}(\alpha\hat{v}_b) \quad (58)$$

$$cl_b^2\left(\alpha\frac{\partial^2\bar{u}_L}{\partial y^2} + \frac{\partial\alpha}{\partial y}\frac{\partial\bar{u}_L}{\partial y}\right) + \alpha q_g = 0 \quad (64)$$

$$\alpha = K_1 y^{-K_0+1}\left(1 - \frac{y}{\delta}\right)^{K_0} \quad (74)$$

$$K_0 = \frac{9\kappa_1^3 U_\tau g}{2cv_L^3}\left(\frac{d_b}{a}\right)^4 \quad (75)$$

$$\kappa_1 = \kappa - \kappa_2 \quad (34)$$
$$= \kappa - \left(\frac{v_L/U_\tau}{d_b/a}\right)^2 \alpha_w.$$

6. A method according to claim 5, wherein said constant $K_0$ is determined from said experimentally-obtained void fraction distribution pattern under stability conditions: to produce non-divergence in said governing equation; and to minimize a sum of the kinetic energy of bubbly flow, with consideration for suppressing the turbulent flow, and potential float energy of bubbly flow.

* * * * *

UNITED STATES PATENT AND TRADEMARK OFFICE
CERTIFICATE OF CORRECTION

PATENT NO. : 6,324,480 B1
DATED : November 27, 2001
INVENTOR(S) : Takahashi et al.

It is certified that error appears in the above-identified patent and that said Letters Patent is hereby corrected as shown below:

Column 2,
Line 14, please delete "$\lambda_m \ v_L/U_\tau$" and insert therefor -- $\lambda_m \propto v_L/U_\tau$ --;

Line 17, please delete "a";

Line 18, please delete "$y/y^+ \ \delta$" and insert therefor -- $y/y^+ \propto \delta$ --;

Line 52, please delete "to a a local" and insert therefor -- to a local --;
Line 67, please delete "$\Delta R_v ,$" and insert therefor -- $\Delta R_v$ --;

Column 3,
Line 11, please delete "$\alpha_L,$" and insert therefor -- $v_L$, --;

Column 4,
Line 11, please delete "$v_L/U_\pi$" and insert therefor -- $v_L/U_\tau$ --;

Column 6,
Line 28, please delete "A";

Column 7,
Line 4, after "bar-crown" please insert -- ¯ --;
Line 56, please delete "$T\omega_L 21 <1 \ (8)$" and insert therefor -- $T\omega_L \ll 1 \ (8)$ --;
Line 58, please delete "$T\omega_L 22 >1 \ (10).$" and insert therefor -- $T\omega_L \gg 1 \ (10).$ --;

Column 8,
Line 32, please delete "do" and insert therefor -- $d_b$ --;
Line 55, please delete "$T^2_{*L}$" and insert therefor -- $T_{*L}^2$ --;

Column 9,
Line 6, please delete "$\tau_t$" and insert therefor -- $\tau_t =$ --;

Column 10,
Line 5, please delete "=" and insert therefor -- ≈ --;
Line 5, please delete "$l^2_{m0}$" and insert therefor -- $l_{m0}^2$ --;
Line 7, please delete "=" and insert therefor -- ≈ --;
Line 15, please delete "$\tau_i$" and insert therefor -- $\tau_t$ --;

UNITED STATES PATENT AND TRADEMARK OFFICE
CERTIFICATE OF CORRECTION

PATENT NO.   : 6,324,480 B1
DATED        : November 27, 2001
INVENTOR(S)  : Takahashi et al.

It is certified that error appears in the above-identified patent and that said Letters Patent is hereby corrected as shown below:

Column 11,
Line 5, please delete "Y" and insert therefor -- $y$ --;
Line 30, please delete "$d_b$/a" and insert therefor -- $d_b/a$ --;

Column 13,
Line 14, please delete "$-\frac{1}{\kappa_1}\left(1 - \sqrt{\frac{C_{f0}}{C_f}} + \left(\frac{1}{\kappa_1} - \frac{1}{\kappa}\right)\log\delta_0^+\right)$"

and insert therefore -- $-\frac{1}{\kappa_1}\left(1 - \sqrt{\frac{C_{f0}}{C_f}}\right) + \left(\frac{1}{\kappa_1} - \frac{1}{\kappa}\right)\log\delta_0^+$ --;

Line 40, please delete "$v_L$=v where $v_L$" and insert therefore -- $v_L=v$ where $v_L$ --;
Line 41, please delete "v" and insert therefor -- $v$ --;

Column 14,
Line 12, please delete "0.5 U" and insert therefor -- 0.5 $U$ --;
Line 30, please delete "a";
Line 53, please delete "skin-fiction" and insert therefor -- skin-friction --;

Column 16,
Line 18, please delete "X-direction" and insert therefor -- x-direction --;
Line 19, please delete "BD" and insert therefor -- CD --;
Line 20, please delete "CD" and insert therefor -- BC --;
Line 63, please delete "$\frac{\partial}{\partial x}(\alpha \bar{v}_L) = O\left(\frac{1}{Re^{11/10}}\right) \approx 0$"

and insert therefore -- $\frac{\partial}{\partial x}(\alpha \bar{v}_b) = O\left(\frac{1}{Re^{11/10}}\right) \approx 0$ --;

Column 17,
Line 16, please delete "$cl_b^2\left(\alpha \frac{\partial \bar{u}_L}{\partial y^2} + \frac{\partial \alpha}{\partial y}\frac{\partial \bar{u}_L}{\partial y}\right) + \alpha q_g = 0$"

and insert therefore -- $cl_b^2\left(\alpha \frac{\partial^2 \bar{u}_L}{\partial y^2} + \frac{\partial \alpha}{\partial y}\frac{\partial \bar{u}_L}{\partial y}\right) + \alpha q_g = 0$ --;

UNITED STATES PATENT AND TRADEMARK OFFICE
CERTIFICATE OF CORRECTION

PATENT NO. : 6,324,480 B1
DATED : November 27, 2001
INVENTOR(S) : Takahashi et al.

It is certified that error appears in the above-identified patent and that said Letters Patent is hereby corrected as shown below:

Column 19,
Line 8, please delete "($d_b$/a)." and insert therefor -- ($d_b/a$). --;
Line 60, please delete "Equation" and insert therefor -- Equations --;

Column 23,
Line 10, please delete "r," and insert therefor -- $\tau_t$ --;
Line 16, please delete "constants" and insert therefor -- constant --;

Columns 23 and 24,
Equation (3), please delete " $\dfrac{\hat{x}}{\hat{u}'_L} = \dfrac{1}{\sqrt{1+T^2\omega_L^2}} = G_x$ "

and insert therefore -- $\dfrac{\hat{x}}{\hat{u}_L} = \dfrac{1}{\sqrt{1+T^2\omega_L^2}} = G_x$ --;

Equation (16), please delete "$\epsilon_L T$" and insert therefor -- $v_L T$ --;

Column 25,
Line 23, please delete "a," and insert therefor -- $\alpha$, --;

Column 26,
Line 19, "$\partial j_x$" and insert therefor -- $\partial j_y$ --; and Line 38, please delete "$\alpha_w$." and insert therefor -- $\alpha_w$ --.

Signed and Sealed this

Twenty-third Day of July, 2002

*Attest:*

*Attesting Officer*

JAMES E. ROGAN
*Director of the United States Patent and Trademark Office*